United States Patent
Gunn et al.

(10) Patent No.: US 7,741,605 B2
(45) Date of Patent: Jun. 22, 2010

(54) METHOD AND APPARATUS FOR DETECTING GAS CONVEYED BY DRILLING FLUIDS

(75) Inventors: Scott Edwin Gunn, Calgary (CA); John Wesley Debliek, Calgary (CA)

(73) Assignee: Varco I/P, Inc., Houston, TX (US)

( * ) Notice: Subject to any disclaimer, the term of this patent is extended or adjusted under 35 U.S.C. 154(b) by 501 days.

(21) Appl. No.: 11/664,892

(22) PCT Filed: Jul. 19, 2005

(86) PCT No.: PCT/GB2005/050113

§ 371 (c)(1),
(2), (4) Date: Apr. 6, 2007

(87) PCT Pub. No.: WO2006/097670

PCT Pub. Date: Sep. 21, 2006

(65) Prior Publication Data

US 2009/0008560 A1    Jan. 8, 2009

(51) Int. Cl.
*G01J 5/02* (2006.01)
(52) U.S. Cl. .................... 250/343; 250/269.1
(58) Field of Classification Search ............ 250/339.13, 250/343, 269.1, 269.2
See application file for complete search history.

(56) References Cited

U.S. PATENT DOCUMENTS

| | | | | |
|---|---|---|---|---|
| 3,727,050 A | * | 4/1973 | Kerr | 250/343 |
| 5,332,901 A | * | 7/1994 | Eckles et al. | 250/345 |
| 5,542,285 A | * | 8/1996 | Merilainen et al. | 73/23.21 |
| 5,716,506 A | * | 2/1998 | Maclay et al. | 204/424 |
| 5,747,809 A | * | 5/1998 | Eckstrom | 250/345 |
| 6,061,141 A | * | 5/2000 | Goldenberg et al. | 356/437 |
| 6,114,700 A | * | 9/2000 | Blades | 250/343 |
| 6,218,662 B1 | * | 4/2001 | Tchakarov et al. | 250/256 |
| 6,388,251 B1 | * | 5/2002 | Papanyan | 250/269.1 |
| 2001/0015408 A1 | * | 8/2001 | Stock | 250/338.5 |
| 2002/0043620 A1 | * | 4/2002 | Tchakarov et al. | 250/269.1 |
| 2004/0010587 A1 | * | 1/2004 | Altamirano et al. | 709/224 |

* cited by examiner

*Primary Examiner*—David P Porta
*Assistant Examiner*—Marcus H Taningco
(74) *Attorney, Agent, or Firm*—Williams, Morgan & Amerson, P.C.

(57) ABSTRACT

A method of detecting gas conveyed in a drilling fluid (M) returning from a well (26), which method comprises the steps of:
(a) extracting gas from said drilling fluid (M);
(b) transmitting infra-red radiation through said gas; and
(c) detecting with a detector (50) infra-red red radiation that has passed through said gas and providing an output signal representative thereof;
characterised by the step of:
(d) examining the intensity of a portion of the infra-red spectrum within a range of approximately 3.1 μm and 3.6 μm to estimate whether or not said gas comprises any light or heavy hydrocarbons.

10 Claims, 13 Drawing Sheets

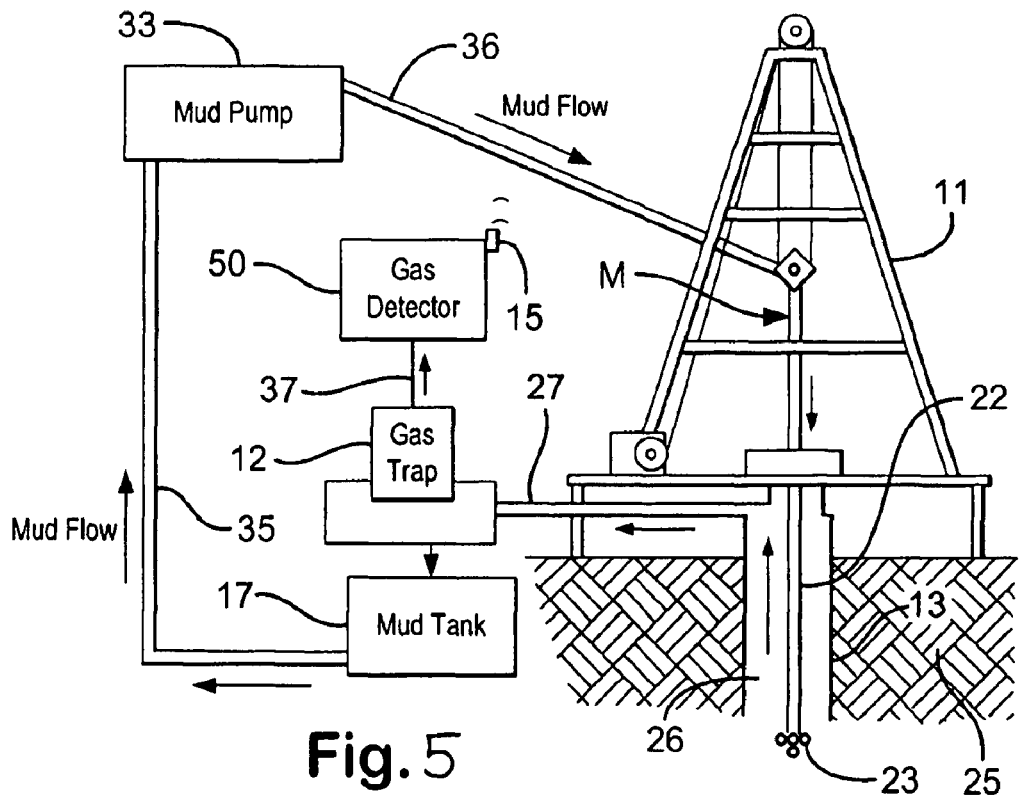
Fig. 5
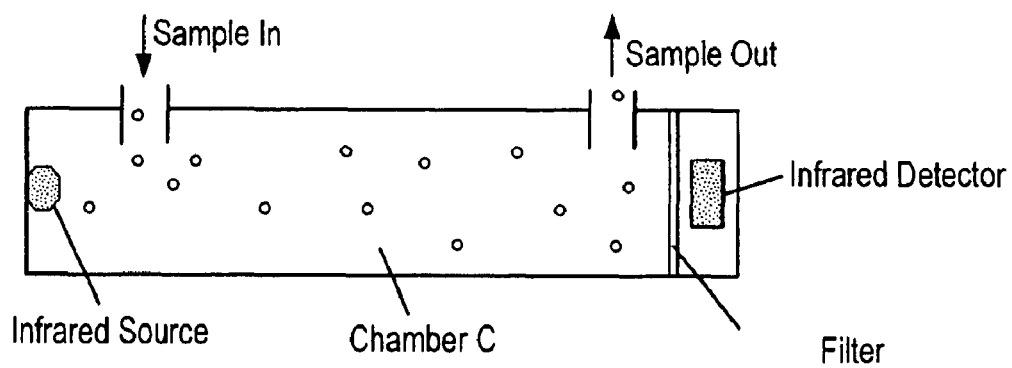
Fig. 6 *Prior Art*
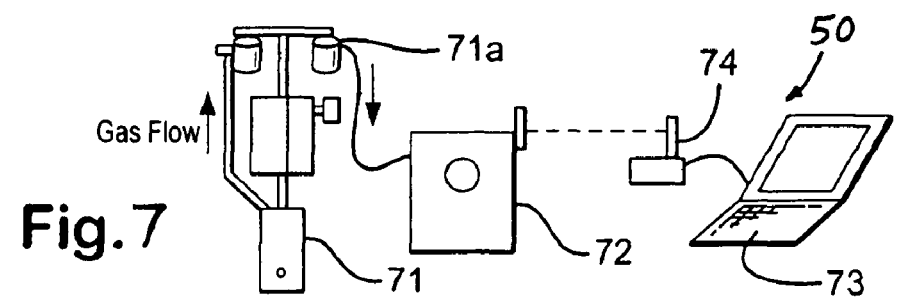
Fig. 7

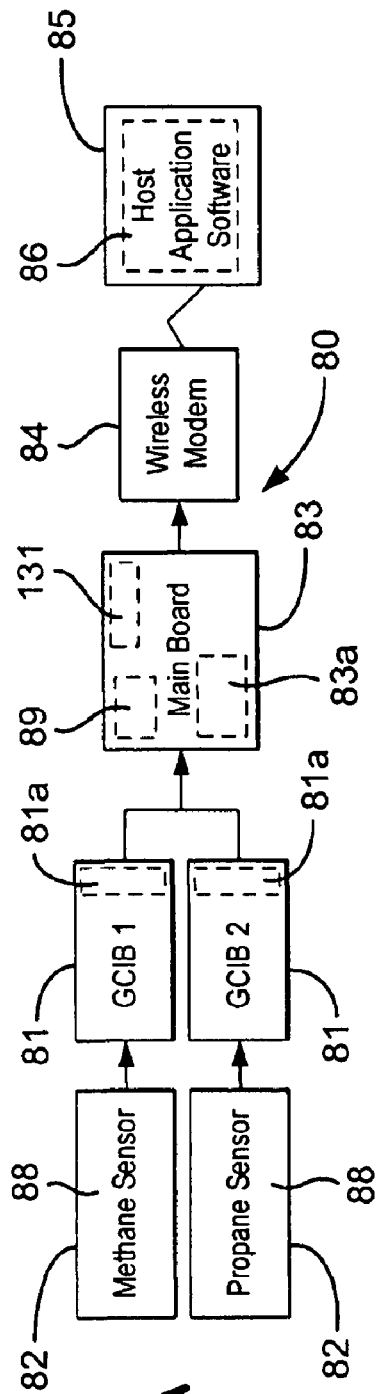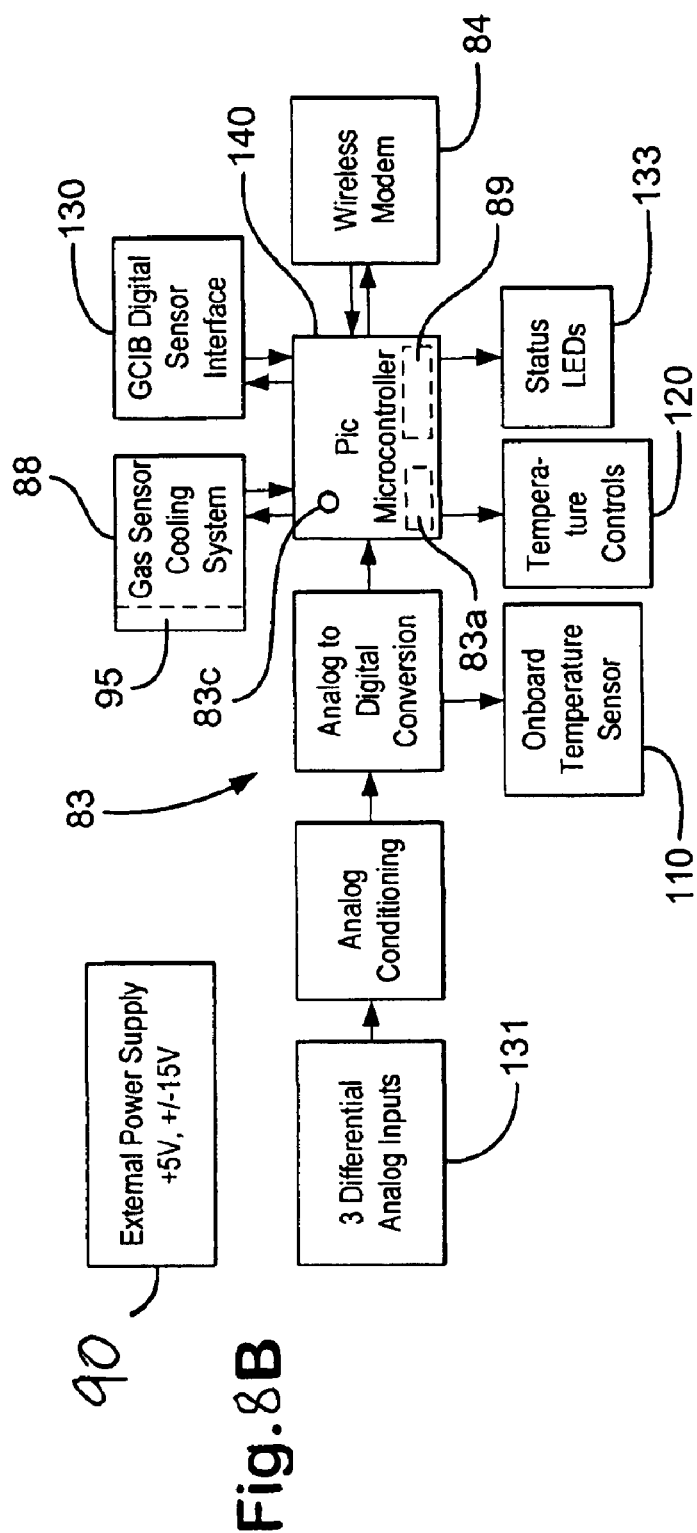
Fig. 8A
Fig. 8B

METHOD AND APPARATUS FOR DETECTING GAS CONVEYED BY DRILLING FLUIDS

The present invention relates to a method for detecting gas conveyed by drilling fluids, an apparatus for performing the method, and to a method of calibrating the apparatus.

During a drilling operation, drilling fluid (or "mud") is continuously pumped down through the drill string and into the region around the drill bit and then back up a borehole annulus to the surface. Often the mud is made up of clays, chemical additives and an oil or water base and performs several important functions. The primary function of the mud is to cool and lubricate the drill bit, carry drill cuttings back up out of the well, and maintain a hydrostatic pressure which prevents pressurized fluids in the earth formation from blowing out through the borehole.

Thus the drilling mud passes from an area of low pressure at or near the surface, to an area of comparatively high pressure adjacent the formation being drilled. Hydrocarbon gases under pressure in the formation become entrained in the drilling fluid as it passes the drill bit; the amount of gas conveyed in the mud is proportional to the pore pressure in the section being drilled. Therefore the drilling fluid performs an important secondary function by carrying information back to the surface about the nature of the formation being drilled.

As the drilling fluid returns to the surface (i.e. an area of lower pressure) these hydrocarbon gases are released. By examining the quantity and type of gas released the petroleum geologist may determine how feasible it is to obtain oil and/or gas from the well.

Gas is typically extracted from the mud by mechanical agitation in a gas trap which is located in a possum belly tank (also called "header tank") or in a box of a shale shaker. The extracted gas is analyzed for hydrocarbons and/or total gas content using one or more of several different detectors such as catalytic combustion detectors (CCD), thermal conductivity detectors (TCD), and flame ionization detectors (FID). Separation and quantification of the different hydrocarbon (e.g. methane through pentanes) gases are then typically carried out via gas chromatography techniques with similar or different detectors.

Due to their relatively low cost and established reputation in the field, apparatus employing TCDs have been used in the oil and gas industry since the 1950s. Five major problems with TCDs are: (1) the output only provides an indication of total gas, by which is meant that an output from the TCD does not differentiate between hydrocarbons; (2) that the detector reacts with the hydrocarbon gases and moisture, and/or becomes dirty, affecting calibration, sensitivity and repeatability (several diesel-based and polymer-type mud systems used on drilling rigs will release small particles into the gas/air sample; these particles may react with the compound forming the detector and corrode it); (3) limited durability as a result of (2), often requiring replacement every 30 days or so; (4) temperature dependence resulting in zero drift and therefore inaccurate results (many oil rigs work in environments with very large diurnal temperature ranges; as such, temperature independence is extremely important); and (5) TCDs are sensitive to hydrogen sulphide, nitrogen and carbon dioxide resulting in a false positive.

U.S. Pat. No. 4,635,735 attempts to address problem (1) above by using infra-red spectrophotometers. Gas extracted from the drilling mud is passed through a series of cells. Each cell comprises an infra-red source and detector at opposing ends of a gas cell. Each detector is tuned to detect a different constituent of the sample gas. Absorptive filters (not specified) are used to select specific wavelengths as follows:

| | |
|---|---|
| Methane: | 7.7 µm |
| Ethane: | 12.0 µm |
| Propane: | 9.5 µm |
| Isobutane: | 8.5 µm |
| Butane: | 10.4 µm |
| Neopentane: | 7.9 µm |

As shown in FIG. 1 U.S. Pat. No. 4,635,735 uses a part of the IR spectrum (6-14 µm) in which peaks of the absorption spectra of the various hydrocarbons are quite well separated. Unfortunately the level of absorption is low in this spectral region, with methane having the strongest absorbance of $8 \times 10^{-4}$. Whilst this problem can addressed to some extent by increasing the distance between the emitter and detector, the IR source output power would need to be higher to compensate; however there is presently a lack of suitable mid-IR sources with such power. Even if there were suitable mid-IR sources this higher power would generate more heat which might interfere with the detector. Furthermore the apparatus would become less sensitive to small changes in the percentage of each gas: the response of the IR detector will tend toward either a zero or maximum output state. Accordingly any increase in the power and size requirements of such an apparatus are highly undesirable.

Accordingly there is a need for a more reliable apparatus for identifying constituents of sample gas from drilling mud. In particular there is need to distinguish between light and heavy hydrocarbon gases carried by drilling fluid returning from a well, and to provide and indication of how much of those gases are present, if any. Furthermore, it would be desirable if such apparatus were lighter and less bulky than prior apparatus.

There are other parts of the IR spectrum in which hydrocarbon gases have absorption spectra. Referring to FIGS. 2 and 3 spectra between 1.6-1.9 µm and 2.0-2.8 µm are shown. In these regions the problem is worse: the absorbances are low and the spectra overlap one another more than in the 6-14 µm range. Referring to FIG. 4 spectra between 3.1 µm and 3.6 µm range are shown. Here the absorbance by each hydrocarbon is stronger by approximately two orders of magnitude making it superficially attractive for detection purposes. However, whilst part of the methane absorption spectrum is relatively isolated, the spectra of the remaining hydrocarbons (ethane, propane, butane, pentane) overlap one another.

According to the present invention there is provided a method of detecting gas conveyed in a drilling fluid returning from a well, which method comprises the steps of:

(a) extracting gas from said drilling fluid;

(b) transmitting infra-red radiation through said gas; and (c) detecting with a detector infra-red red radiation that has passed through said gas and providing an output signal representative thereof;

characterised by the step of:

(d) examining the intensity of a portion of the infra-red spectrum within a range of approximately 3.1 µm and 3.6 µm to estimate whether or not said gas comprises any light or heavy hydrocarbons. A particular advantage of this method is that hydrogen sulphide, nitrogen and carbon dioxide will not affect the output signal. In one aspect said portion comprises a range of approximately 3190 nm to 3540 nm. In one embodiment two different portions are examined: one portion comprising an absorption spectrum of one or more light hydrocarbon, and the other portion comprising an absorption spectrum of one or more heavy hydrocarbon. This enables a distinction to be made between methane and propane for example, as well as a total gas (percentage by volume) indication of all detectable hydrocarbons.

Preferably, said portion comprises part of an absorption spectrum of a light hydrocarbon.

Advantageously, said portion comprises an upper wavelength limit of approximately 3330 nm to reduce detection of heavy hydrocarbons.

Preferably, said portion comprises a lower wavelength limit of approximately 3190 nm.

Advantageously, said portion comprises part of an absorption spectrum of a heavy hydrocarbon.

Preferably, said portion comprises a lower wavelength limit of approximately 3340 nm to reduce detection of light hydrocarbons.

Advantageously, said portion comprises an upper wavelength limit of approximately 3540 nm.

Preferably, the method further comprises the step of filtering said infra-red radiation such that substantially only said portion reaches said detector.

Advantageously, the method further comprises the steps of transmitting infra-red light through said gas over a first path and over a second path shorter than said first path, and outputting a signal representing the intensity of infra-red light received over each path. The path lengths are different according to the hydrocarbon(s) to be detected: where absorbance is lower, a longer path length should be used.

Preferably, the method further comprises the step of examining a first portion in said range for infra-red light received on said first path, and a second portion in said range for infra-red light received on said second path, wherein said first and second portions are different to distinguish between any light and heavy hydrocarbons in said gas.

Advantageously, the method further comprises the steps of measuring said intensity with a pyroelectric detector.

Preferably, the method further comprises the step of substantially thermally isolating said pyroelectric detector from said gas, whereby the effect of pressure and/or temperature variation of said gas on said output signal is reduced.

Advantageously, (b) comprises the step of driving an infra-red emitter in a cyclical manner so as to produce pulses of infra-red radiation, whereby a cyclical output voltage corresponding to said pulses is obtained from said detector the magnitude of which represents the intensity of infra-red radiation received by said detector.

Preferably, said driving step comprises driving said infra-red emitter with a 50% duty cycle, whereby an output from said infra-red detector is substantially sinusoidal. This provides a useful input signal to an electronic signal conditioning part of the apparatus.

Advantageously, the method further comprises the step of converting said cyclical output voltage to DC, the magnitude of which is proportional to the amount light or heavy hydrocarbon present in said gas.

Preferably, the method further comprises the step of outputting a reference channel, which reference channel represents an infra-red radiation intensity at a wavelength outside said range, whereby said reference channel may be used to adjust said output signal such that it is substantially temperature invariant.

Advantageously, the method further comprises the step of subtracting said reference channel from said output signal to remove any temperature transients therefrom.

Preferably, the method further comprises the step of multiplying said reference channel by a scaling factor before said subtraction step to compensate for any difference in response of said detector and said reference channel to temperature variation.

Advantageously, the method further comprises the step of converting said output signal to into a volume signal that represents the amount of said gas by volume.

Preferably, said conversion step comprises the step of inserting a numerical value representative of said output signal into a conversion formula. This might be by using a computer to calculate a result, or by using a look-up table for example.

Advantageously, the method further comprises the step of using two formulae, one for a first volume range and another for a second volume range.

Preferably, the method further comprises the step of repeating steps (a) to (d) to provide a substantially continuous output signal representing the amount of light and heavy hydrocarbons contained in said drilling fluid.

Advantageously, the method further comprises the step of averaging said output signal over a predetermined time period.

Preferably, the method further comprises the step of transmitting data representing said output signal to a remote host, said data useable by said remote host to display a substantially real-time indication of the amount of light and heavy hydrocarbons present in said drilling fluid and/or a total hydrocarbon gas content present in said drilling fluid. This enables data analysis to be performed away from the hazardous area in the drilling rig.

Advantageously, said transmission step comprises the step of wirelessly transmitting said data to said remote host.

Preferably, said infra-red detector comprises a pyroelectric crystal, said method further comprising the steps of monitoring a temperature environment around said infra-red detector, and heating or cooling said environment according to said temperature.

Advantageously, said light hydrocarbon comprises methane and/or ethane.

Preferably, said heavy hydrocarbon comprises propane and/or butane and/or pentane.

According to another aspect of the present invention there is provided an apparatus for detecting gas conveyed in a drilling fluid returning from a well, which apparatus comprises an infra-red emitter, a first infra-red detector and a chamber therebetween, the arrangement being such that, in use, infra-red radiation is passed through gas in said chamber and said first infra-red detector provides an output signal representative of the intensity thereof, characterised by a filter for selecting a portion of the infra-red spectrum within a range of approximately 3.1 µm and 3.6 µm, examination of said portion facilitating detection of light and/or heavy hydrocarbon in said gas. The apparatus can be used with a variety of gas traps and can thus be retrofit.

Advantageously, wherein in use said filter selects a portion comprising part of an absorption spectrum of a light hydrocarbon.

Preferably, wherein in use said filter selects a portion comprising part of an absorption spectrum of a heavy hydrocarbon.

Advantageously, said filter comprises a physical filter.

Preferably, said physical filter comprises a passband filter for passing substantially only said portion.

In one embodiment said physical filter comprises quartz.

Advantageously, said first infra-red detector comprises a first pyroelectric crystal, the arrangement being such that, in use, said filter passes substantially only said portion, and said first pyroelectric crystal generates an output voltage proportional to the intensity of infra-red radiation in said portion.

Preferably, said apparatus further comprises a second infra-red detector providing a reference channel to compensate said output signal from said first infra-red detector for temperature.

Advantageously, said apparatus further comprises a reference channel filter for passing to said second infra-red detector a reference portion of the spectrum outside said range, which reference portion comprises wavelengths substantially unaffected by the presence of said hydrocarbons.

Preferably, said reference channel filter comprises sapphire.

Advantageously, said apparatus further comprises a secondary filter for substantially thermally isolating for said first infra-red detector.

Preferably, said apparatus further comprises a first chamber and a second chamber, each chamber having a respective infra-red detector and filter, wherein said filters are different for passing a first portion and a second portion in said wavelength range, said first portion comprising part of an absorption spectrum of a light hydrocarbon and said second portion comprising part of an absorption spectrum of a heavy hydrocarbon, the arrangement being such that, in use, said output signal represents the amount of light hydrocarbon present in said first chamber and the amount of heavy hydrocarbon in said second chamber.

Advantageously, said first chamber has a length longer than a length of said second chamber. In one embodiment said first chamber has a length of about 25.4 mm (1") and said second chamber has a length of about 12.7 mm (0.5").

Preferably, said apparatus further comprises a gas inlet to and an gas outlet from said first and second chambers and a port therebetween, the arrangement being such that, in use, gas flows through said gas inlet for testing in said first or second chamber, through said port for testing in the other of said chambers, and out of said gas outlet, whereby substantially continuous detection of gas returned in said drilling fluid may be made.

Advantageously, said apparatus further comprises a block of material in which said first infra-red emitter, said infra-red detector, said chamber and said filter are mounted, said block of material having thermal conductivity higher than about 200 W m$^{-1}$ K$^{-1}$.

In one embodiment said block comprises aluminium.

Preferably, said apparatus comprises a heating element for heating said block to maintain the temperature of said infra-red detector substantially constant.

Advantageously, said apparatus comprises a cooling element for cooling said block to maintain the temperature of said infra-red detector substantially constant.

Preferably, said apparatus comprises a case having a gas inlet, a gas outlet, and a power supply port, whereby said apparatus is portable for emplacement on a drilling rig the arrangement being such that, in use, said gas inlet is connectable to a gas trap for receiving gas conveyed in said drilling fluid.

Advantageously, said apparatus comprises a case heating device for heating the volume enclosed by said case.

Preferably, said apparatus comprises a case cooling device for cooling the volume enclosed by said case.

Advantageously, said apparatus comprises a wireless transmitter for transmitting said output signal to a remote host, whereby said apparatus may be placed adjacent a shale shaker for receiving gas entrained by said drilling fluid and said output signal may be transmitted to said remote host substantially in real-time.

According to another aspect of the present invention there is provided a method of calibrating an apparatus as set out above, which method comprises the steps of:

(a) passing different concentrations of gas through said apparatus;

(b) recording in a computer memory results of the output signal for each concentration of gas;

(c) fitting a polynomial to results for a light hydrocarbon gas, and fitting different polynomials to results of different concentrations for a heavy hydrocarbon gas; and (c) storing said polynomials in a computer memory.

Preferably, step (d) comprises the step of storing said polynomials in computer memory on a remote host.

Advantageously, step (d) comprises the step of storing said polynomials in computer memory on said apparatus.

The present invention, in at least certain embodiments, discloses a gas detection system which includes infra-red gas detector apparatus that is specific to hydrocarbon components through which a sample gas flows, a computer system for receiving data from the infra-red gas detector apparatus and for processing such data, a display (e.g. screen and/or strip chart) to display results (in one aspect, in real time) and, optionally, connections and interfaces for providing test results at sites remote from the test site. In certain aspects, the present invention discloses a method for detecting gas in a fluid, the method including flowing fluid bearing gas through a gas trap apparatus; flowing gas trapped by the gas trap apparatus to and through an infra-red gas detection system for detecting the gas, the infrared gas detection system having a first processor and apparatus for isolating absorption spectra of the gas; producing with the infra-red gas detection system analogue signals indicative of levels of the gas; converting the analogue signals to digital signals with the first processor; transmitting the digital signals from the first processor to a second processor; and producing with the second processor digital signals indicative of the level of gas. In certain aspects, the present invention discloses a system for detecting gas in a fluid, the system including an enclosure; an infra-red gas sensor apparatus within the enclosure; an interface board apparatus within the enclosure and in communication with the infra-red gas sensor apparatus; analogue signal apparatus in the infra-red gas sensor apparatus for producing analogue signals indicative of a level of gas in a fluid; conversion apparatus on the interface board apparatus for converting the analogue signals to digital signals; and transmission apparatus on the interface board apparatus for transmitting the digital signals to a host system.

In one particular aspect, a gas detection system according to the present invention has a methane sensor and a propane sensor, each of which is connected to a corresponding gas chamber interface board (GCIB). The GCIB's provide an interface between the sensors and a drive for an infra-red lamp (one lamp in each sensor); and each GCIB performs amplification and signal conditioning on the sensor output signals and does an analogue-to-digital (A/D) conversion of data from the sensors. By doing this on the GCIB's, susceptibility to noise is reduced. The sensors are calibrated on the basis of the digitized signals (digitized signals produced by the GCIB's), thus the calibration can be handled completely in software.

A WSGD main board contains a primary processor for the system which handles communications and control within the system. The main board reads the digitized data from the GCIB's via a serial interface. In certain aspects, the main board communicates with a host computer (e.g. a desk top or a laptop, on site or remote), in one aspect via a wireless modem. The host computer provides the user interface to the system and performs and displays the calibration of the sensor data and generates results for gas content, e.g. but not limited to, methane and propane content.

Systems according to the present invention can measure levels of hydrocarbons (e.g. methane, ethane, propane, butane, and iso-butane). In one aspect, the sensors are calibrated for 0 to 100% volume of gas in air of methane and propane, however both sensors are sensitive at some level to other hydrocarbons. The sensors in such an embodiment do not completely isolate methane and propane from other hydrocarbons, but rather, the methane sensor provides a stronger response to methane and ethane (see, e.g. curve C1, FIG. 18) and the propane sensor provides a stronger response to propane, butane, and iso-butane (see, e.g. curve C3, FIG. 18). This provides a way to distinguish between light hydrocarbons (methane, ethane) and heavy hydrocarbons (propane, butane, pentane). Systems according to the present invention can be portable with an easily emplaceable lightweight-polyurethane-encased gas trap, in one aspect with a gas dryer; a component-specific infra-red gas detector system, a laptop computer, and a wireless modem. In one particular aspect, using a wireless modem or similar device, a wireless portable gas monitor is provided.

In one particular aspect, an infra-red gas detector system used with systems according to the present invention has a light source and a dual channel infrared detector with a narrow band infrared filter on each channel. In one aspect, the filters are on a sapphire substrate, and an overall quartz window covers the sensor to protect the filter surfaces and provide additional thermal isolation for the sensor. One channel of the detector is used to detect the infrared absorbed by the target gas; the other channel is used as a reference channel to provide compensation of the sensor for temperature and luminance variations. There is never any physical reaction with the gas/air mixture and thus sensor consistency and repeatability does not deteriorate. In certain aspects, routine calibrations of such system can be good for over 6 months. The sensor is sealed in a capsule and quartz window and contaminants in gases have little effect on its sensitivity and repeatability. High levels of humidity can generate false readings on a sensor, so it is preferable, in certain aspects, to filter out moisture from the input gas stream. The sensors use frequency-specific molecular absorption; to indicate hydrocarbons. Particles of mud systems do not react with the sensors and the sensors use filters on the lenses so only the specific frequency for hydrocarbons gases are detected by the sensor. $H_2S$, $N_2$ and $CO_2$ are at different frequencies and are not detected. The sensors, in certain embodiments, indicate methane and propane in their pure form, but can also indicate gases of multi-component composition. In certain aspects, the methane sensor is calibrated for 0 to 100% volume ethane, or the propane sensor is calibrated specifically for 0 to 100% volume butane, isobutane, or pentane. This does not change the response of the sensors to other gases. This gives a geologist a full evaluation of each hydrocarbon-bearing zone and can indicate secondary zones that were not previously considered.

For a better understanding of the present invention reference will now be made, by way of example, to the accompanying drawings in which:

FIG. 5 is a schematic block diagram of an apparatus according to the present invention in use with a well and drilling rig;

FIG. 6 is a schematic side view of a prior art infra-red sensor apparatus;

FIG. 7 is a schematic view of an apparatus according to the present invention in use with a gas trap and a remote host;

FIG. 8A is a schematic block diagram of parts of the apparatus of FIG. 7;

FIG. 8B is a schematic block diagram of electronic components of an apparatus according to the present invention;

Figure 1:
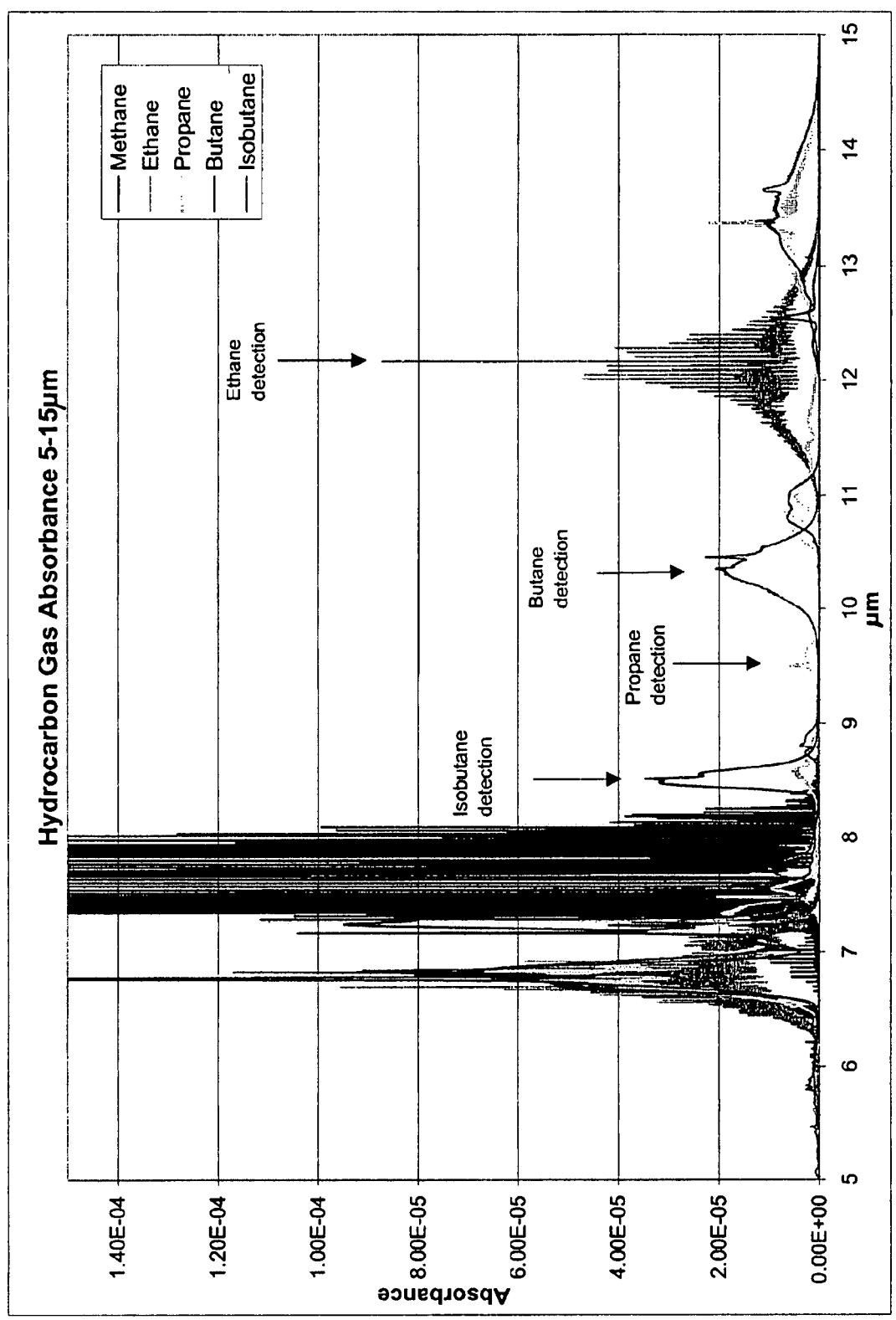
FIG. 1 is a graph of absorbance vs. wavelength for five hydrocarbon gases in the 6-14 μm portion of the spectrum.
Figure 2:
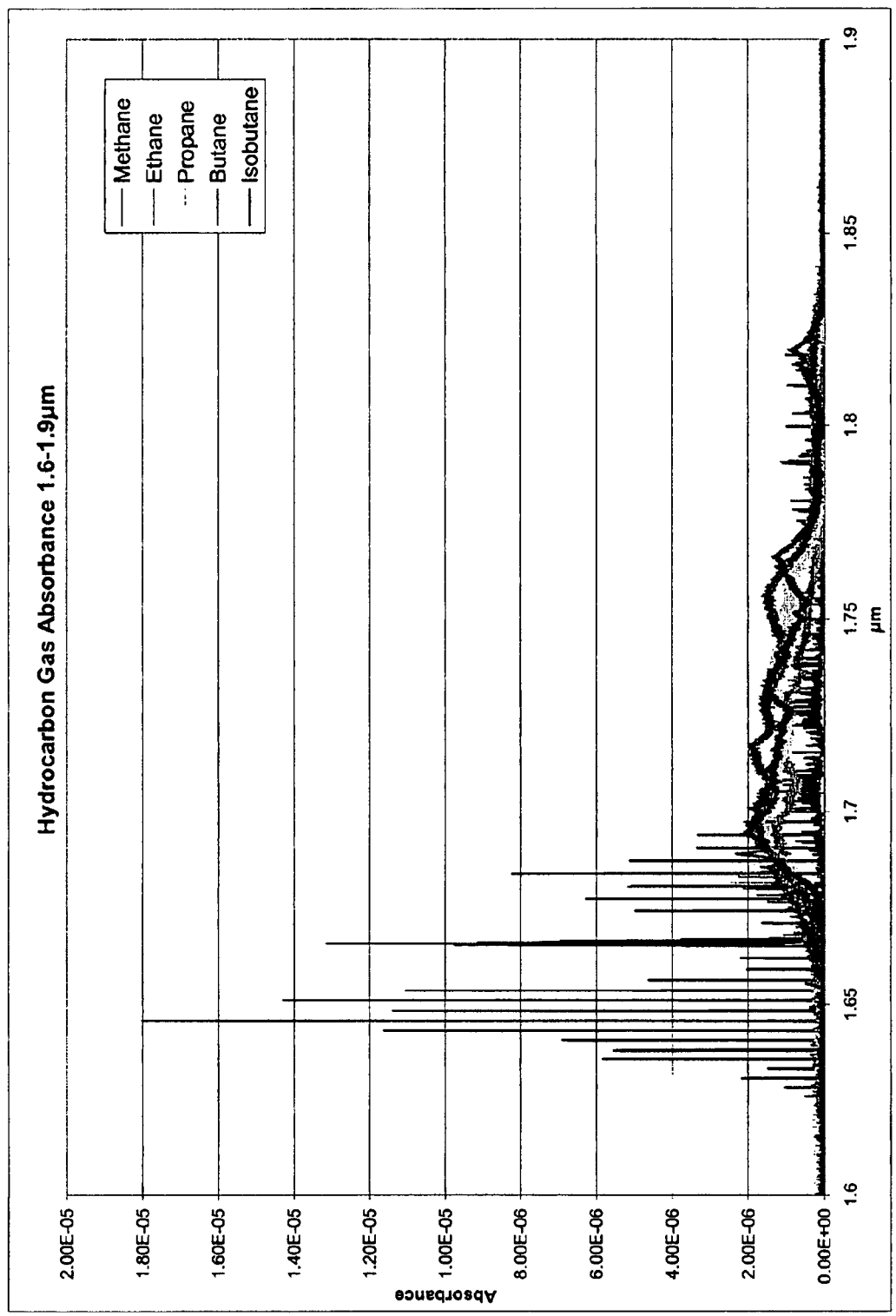
FIG. 2 is a graph of absorbance vs. wavelength for five hydrocarbon gases in the 1.6-1.8 μm portion of the spectrum.
Figure 3:
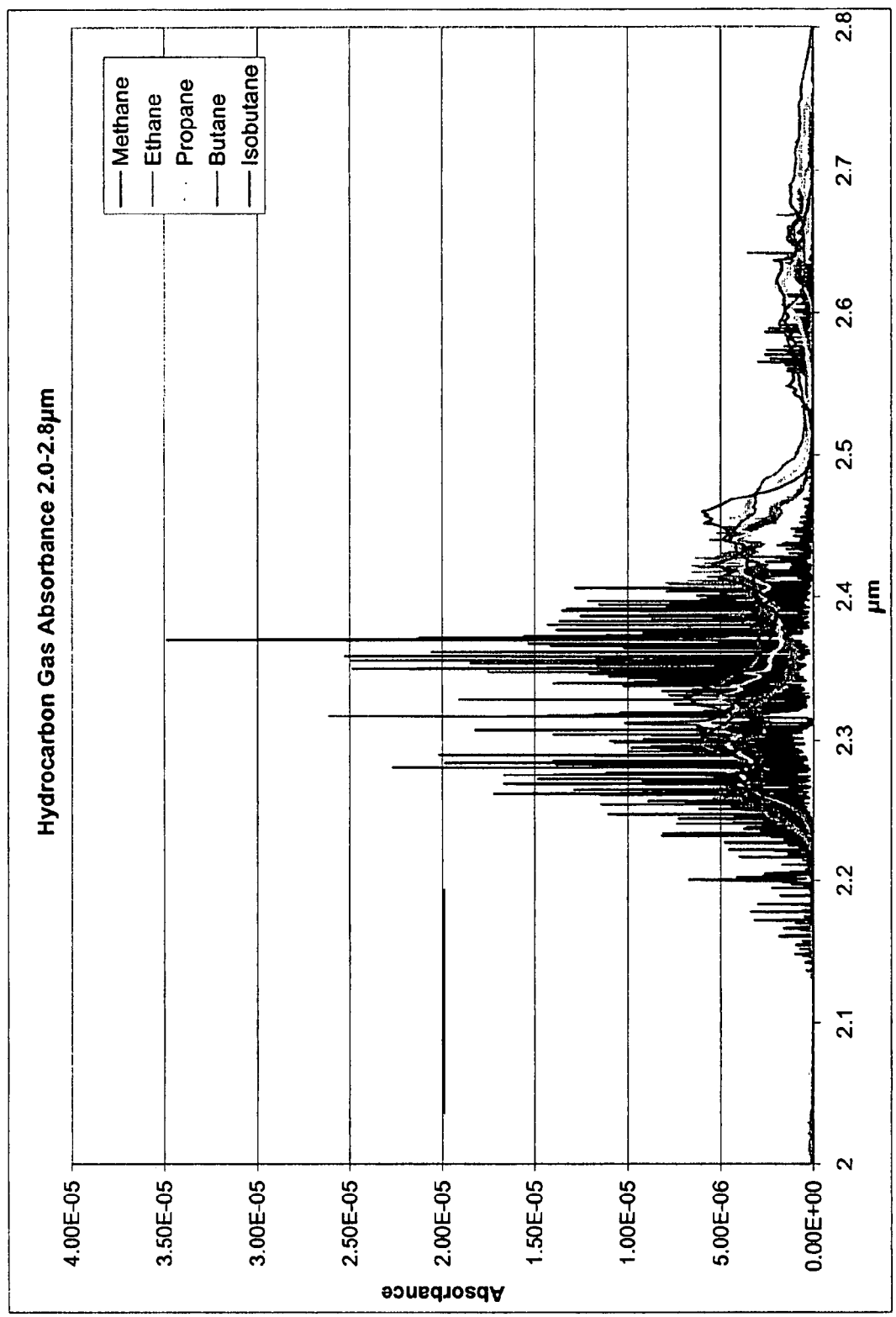
FIG. 3 is a graph of absorbance vs. wavelength for five hydrocarbon gases in the 2.1-2.8 μm portion of the spectrum.

As shown in FIG. 5 a gas detector 50 according to the present invention receives sample gas in a polyurethane ("polyflow") line 37 from a gas trap 12. The gas trap is available from MD Totco, Cedar Park, Tex., U.S.A drilling rig 11 drills a well 13 into a formation 25. A mud pump 33 pumps mud M in a line 36 into the well 13 down a drillstring 22, to and through a bit apparatus 23, and then up in an annulus 26 to an exit line 27 which feeds into the gas trap 12. The mud M exits the gas trap 12 and flows into a mud tank 17 from which the mud pump 33 pumps the mud in a line 35 back to the line 36. A transmitter or modem 15 (e.g. wireless or hardwired) transmits signals from the gas detector 50 to apparatus or systems such as a computer, computer system, network, or a data acquisition system or apparatus.

The gas trap 12 is positioned in the mud box or possum belly of a shale shaker (not shown) i.e. that part of the shale shaker which receives mud M after it returns from the well 13 but before it is processed by the shale shaker. The gas trap 12 is positioned close to the output of the exit line 27, but away from any corners of the mud box where pooling can occur. This helps to ensure that the gas extracted from the mud M represents the most recent drilling downhole.

The gas trap 12 comprises beater bars (not shown) submerged in the mud M. The beater bars are vibrated at 1725 rpm to agitate the mud M and release any entrained gas. As the gas is released it is collected in a chamber above the mud M where it is drawn through a set of dryers (not shown) by a pump. The dryers comprise calcium chloride and ethylene glycol which serve to remove any moisture from the gas. The gas is drawn at atmospheric pressure through the polyurethane line 37 into the gas detector 50 as described in greater detail below.

FIG. 6 shows a typical prior art infra-red sensor system (see e.g. U.S. Pat. No. 4,635,735) in which infra-red light from an infra-red source passes through material to be analyzed in a chamber C, then through an absorptive filter, to an infra-red detector. The material flows into the chamber C through a "Sample In" port and out through a "Sample Out" port.

FIG. 7 shows the gas detector 50 in more detail. It comprises a gas trap 71, a gas dryer 71a, a wireless portable gas monitor 72, a laptop computer 73 (to serve as a remote host with host software), and a wireless radio modem 74. The wireless portable gas monitor 72 comprises an explosion-proof case measuring 0.39 m×0.37 m×0.19 m without a hangar mount (for mounting on a handrail for example) and 0.60 m×0.37 m×0.22 m with a hangar mount; it weighs about 25 kg. Accordingly it is readily moveable by hand. In use sample gas is extracted from mud M by the gas trap 71, drawn by a pump (not shown) to the wireless portable gas monitor 72 for analysis. The output from the wireless portable gas monitor 72 is transmitted wirelessly to the laptop computer 73 where the results are displayed and/or stored in memory as described in more detail below. The small size and wireless communication provided by the wireless portable gas monitor 72 enables it to be placed close to the shaker where gas samples are taken; this has reduced gas to detector travel time to approximately 10 s (distance approximately 6.1 m between gas trap and monitor) as opposed to prior art systems which took between two and five minutes (distance approximately 91-122 m between gas trap and prior art monitors). Accordingly results are provided substantially in real-time to the geologist. Furthermore the geologist does not need to be located in a hazardous area on the drilling rig to analyse results; he could be anywhere in the world and receive the output from the wireless portable gas monitor 72 over the Internet.

Referring to FIG. 8A the wireless portable gas monitor 72 comprises two GCIB's 81 (Gas Chamber Interface Boards) that interface two gas detectors 82. The gas detectors 82 provide analogue data comprising an alternating sinusoidal waveform whose amplitude is reduced by the infrared absorption in the wavelength band of interest. A main board 83 receives digitized data from the GCIB's 81 and, via a wireless modem 84 (or land line) communicates with a remote host 85 (e.g. a computer system). With host application software 86, the remote host 85 provides a graphic presentation of gas levels, e.g. methane and propane levels present in gas passing through the wireless portable gas monitor 72. The detectors 82 are each connected to a GCIB 81 which provides an interface for each detector 82 and a drive for the IR emitter in each gas detector 82. The GCIB's 81 perform amplification and signal conditioning on the sensor output signals (analogue signals indicative of gas level) which, following digitization and calibration indicate actual gas levels (as a % by volume of gas in air) before doing an A/D conversion on board (or off board). By doing the A/D conversions on the GCIB's system susceptibility to noise and temperature induced transients is reduced. Optionally, analogue conditioning is performed. The analogue conditioning performed takes the alternating waveform from the sensor and rectifies and filters it to give a DC voltage output that can be digitized. The waveform is also inverted before digitization so that the signal will actually increase as the gas concentration increases. The calibration of the sensor is performed on the digitized signals, so calibration can be handled completely in software in the remote host 85.

Each GCIB 81 has a small microprocessor that controls the A/D conversion on its board and also handles a serial interface to the main board 83; a digital temperature sensor (not shown) is provided on-board each GCIB 81. The main board 83 has a primary microprocessor 89 which requests sensor and temperature data from the GCIB's, handles temperature control of the system, performs digital processing, (e.g. exponential averaging) on the sensor data, handles timing and control of the system, and provides a serial interface to the wireless modem 84, through which the host application software 86 can remotely issue commands and receive sensor data from the system. The main board 83 also has non-volatile memory 83a to store the calibration data for the system.

Figure 4:
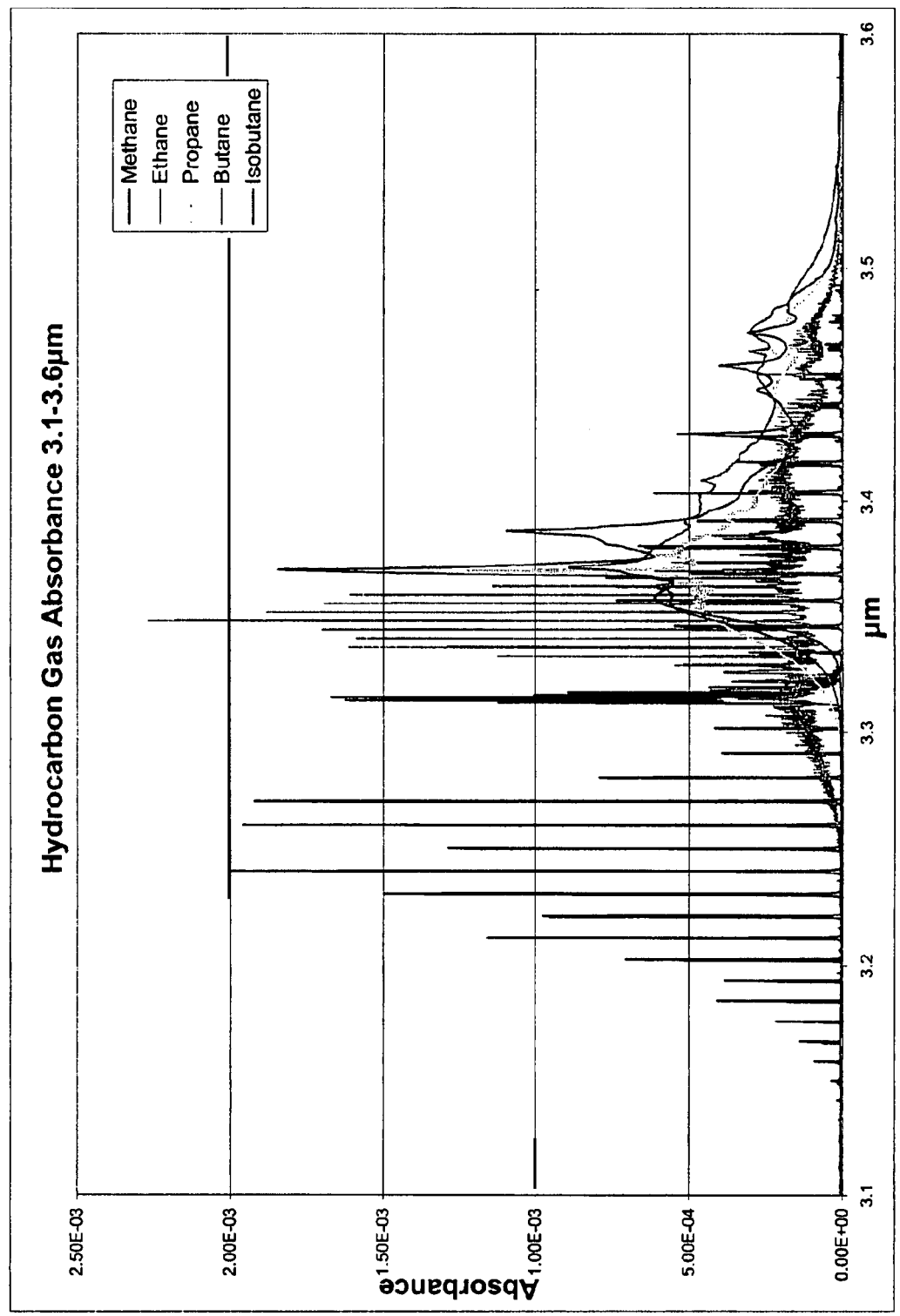
FIG. 4 is a graph of absorbance vs. wavelength for five hydrocarbon gases in the 3.1-3.6 μm portion of the spectrum.

To read sensor data from the GCIB's 81 the main board 83 sends a command to put the GCIB's 81 into a gas sample mode. When the GCIB's 81 receive this command, they perform A/D conversion, e.g. they do 4096 A/D conversions of the sensor signals over a 1.2 second period (five lamp drive pulse periods), and average these to produce an output value for each sensor channel. The main board 83 reads these values after the 1.2 second period. The main board 83 then issues a command to put the GCIB's into a temperature sample mode, and reads the temperature data for each gas detector 82 and each GCIB 81. The temperature data is not averaged on the GCIB, although analogue filtering (to remove higher frequency noise from the signal in order to improve the signal-to-ratio) is performed prior to A/D conversion. The main board 83 reads the data from both gas detectors 82 every two seconds. Some additional exponential averaging may, optionally, be performed on the sensor and temperature data by the main board processor before it is sent to the remote host 85 via the wireless modem 84. Temperature control can also be performed at regular, e.g. two second, intervals. Case heaters 87 (see FIG. 5) are controlled by a temperature sensor (e.g., part of a temperature control system, i.e. the "Temperature Controls" 120, FIG. 4B) on the main board 83. If the temperature reading is lower than the case temperature set point (32 degrees Celsius), heater resistors 105 are turned on for the two second period. The detectors 82 have a heater 87 and a cooler 88 (e.g. a heater and thermal electric cooler, "TEC") to control the sensor temperature. A second order temperature control loop is used to modulate the sensor's heater and cooler to provide greater stability of the sensor temperature. The heater or TEC power is modulated so that the power input is related to the temperature error (differential component) to create a proportional-differential (PD) type of controller.

Data packets comprising sensor data are sent to the host 85 every two seconds. The host application software 86 takes the sensor data and applies calibration data that it has stored in memory for the unit to generate proper gas readings. Alternatively, the host application software 86 can issue commands to read or write the non-volatile memory 83a on the main board 83, allowing the calibration information to be stored in the gas detector on the main board 83 rather than on the remote host 85. When the host application software 86 is started, it requests the calibration information from the main board 83 in the gas detector.

Each GCIB 81 has two sensor input channels, two temperature sensor input channels, and two infra-red source drive outputs. In one aspect the drive outputs are pulsed at a 4.17 Hz rate and the detectors 82 detect the variation in temperature as the lamps are pulsed, creating a small alternating output voltage. A selected narrow band filter filters the infra-red radiation so that the detector receives only a portion of infra-red radiation in a wavelength range of interest (e.g. 3190 to 3330 nm for methane, 3330 to 3540 nm for propane). If a gas with an infrared absorption at that wavelength passes through the sensor, less light will reach the sensor, and it will not see as large a temperature variation, resulting in the amplitude of the output signal decreasing. In one aspect, on the GCIB 81, this signal first goes through a fixed 10 times gain low noise amplifier 81a (see FIG. 4A), followed by a gain stage with selectable 6, 12, 24, or 48 times gain. The signal is then rectified, inverted and filtered (on the GCIB 81) to generate a DC voltage output that increases as the sensor signal decreases due to absorption of the light. There is an offset adjustment to set the base output voltage (similar to the zero adjustment), and there is an output gain adjustment similar to the span adjustment. The adjustments on the GCIB do not do the actual sensor calibration, but rather set up a nominal offset and gain for the sensor such that the output is within a valid operating window. In one aspect, these adjustments on the GCIB 81 are done when a sensor is first connected to the board, after which point calibration is handled through software parameters that are stored in the non-volatile memory 83a on the main board 83 in the wireless gas monitor 72.

Figure 9A:
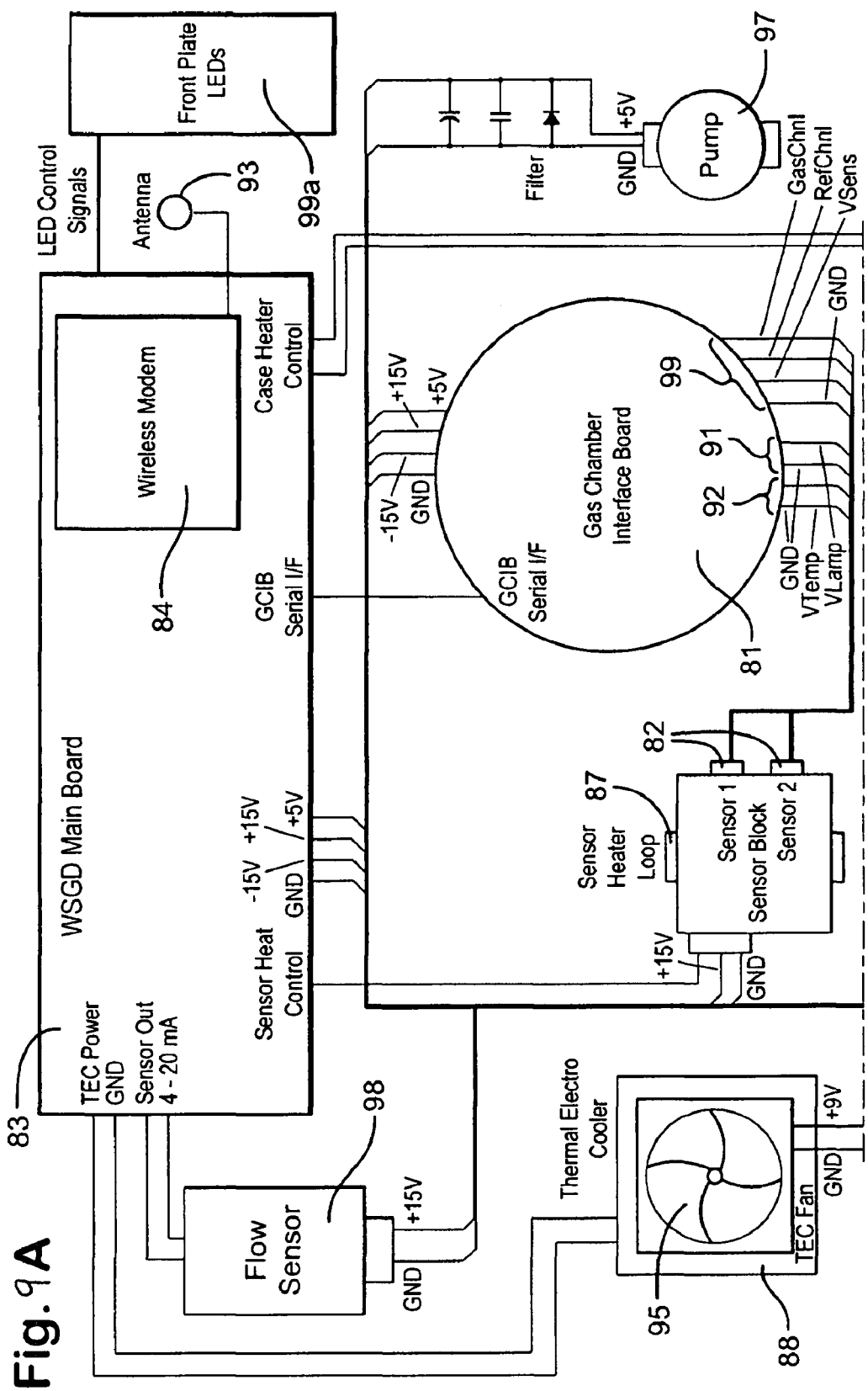
FIGS. 9A and 9B are a schematic block diagram of an apparatus according to the present invention.
Figure 9B:
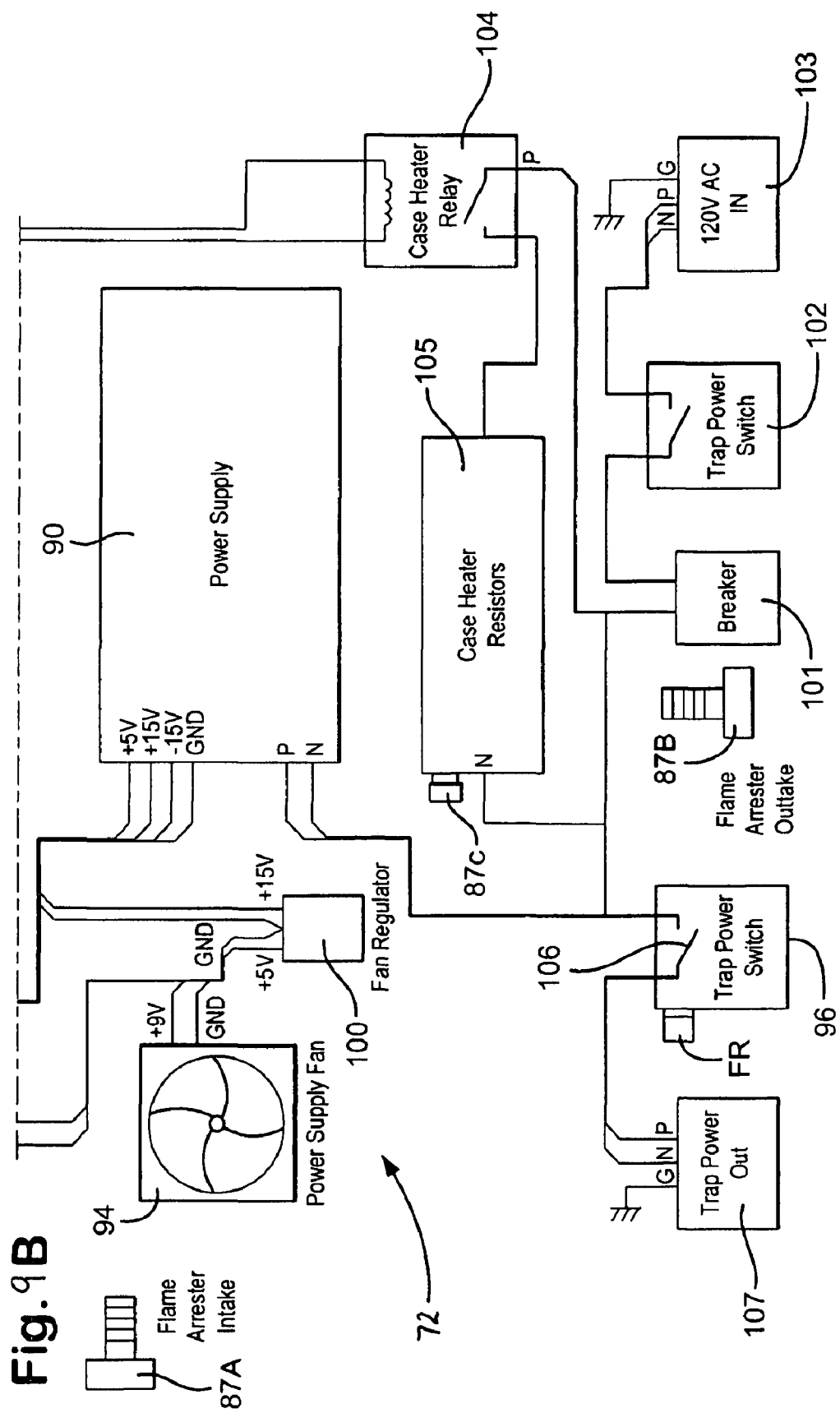
Figure 10:
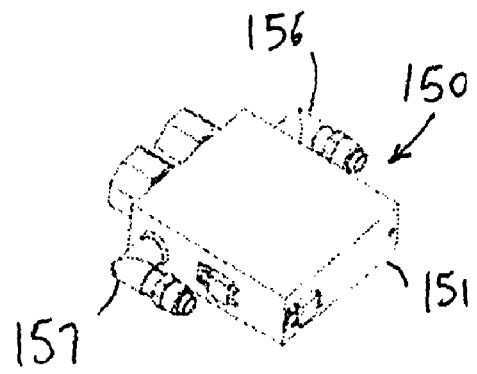
FIG. 10 is a schematic perspective view of a gas sensor apparatus that is part of the apparatus of FIG. 8A.
Figure 11:
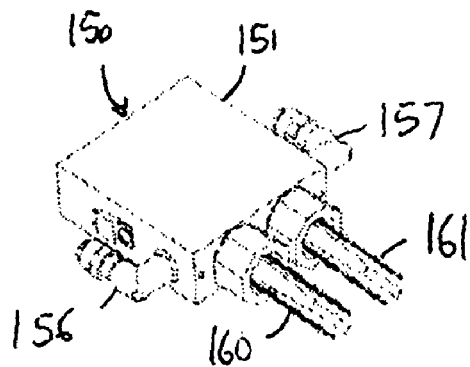
FIG. 11 is a schematic perspective view of the gas sensor apparatus of FIG. 10 connected to input an output gas sample lines.
Figure 12:
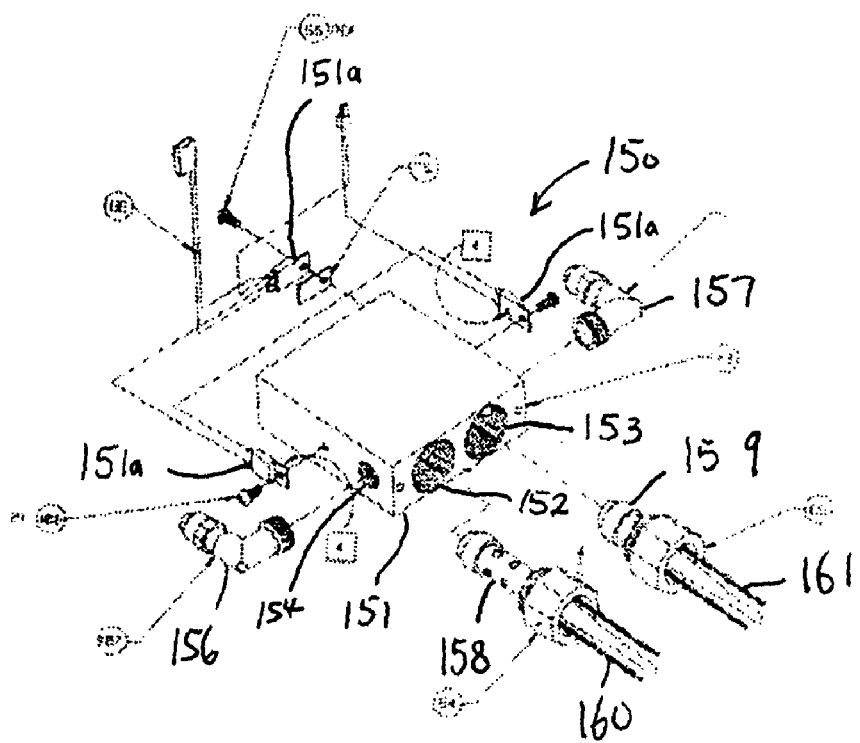
FIG. 12 is an exploded perspective view of the gas sensor apparatus of FIG. 10.
Figure 13:
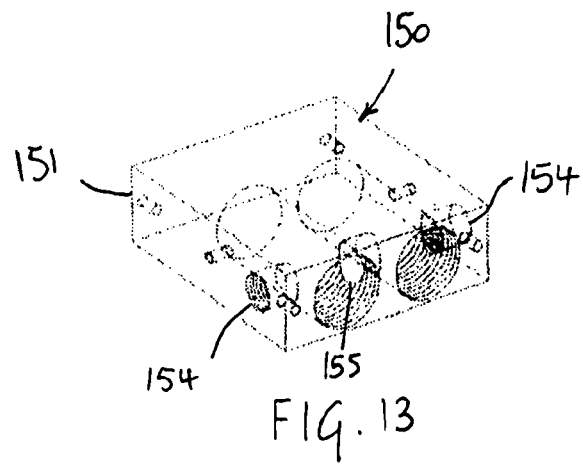
FIG. 13 is a perspective view of a housing part of the gas sensor apparatus of FIG. 10.

As shown in FIGS. 9A and 9B, in the wireless portable gas monitor 72 the wireless modem 84 is connected to an antenna 93. A power supply 90 provides power for the GCIB's 81, the main board 83, the wireless modem 84, the detectors 82, a power supply fan 94, a cooler 88, a pump 97 and an air vacuum transducer (flow sensor) 98. The case heater resistors 105 are controlled by a case heater relay 104 powered from 120 VAC. The case heater relay is used to open and close the circuit to maintain the system within an operational temperature range, e.g. above 25 degrees Celsius. The AC power plug 103, circuit breaker 101, and power switch 102 are for power control protection for the entire unit. Power for a gas trap 96 flows through a switch 106 and a 120 VAC plug 107. Optionally a filter FR filters moisture from the gas. A fan regulator 100 provides 9 VDC current to power the fans.

Referring to FIG. 8B a schematic block diagram of the main board 83 is shown. In one aspect the main board 83 is a PIC micro based data gathering and communications board or card, for receiving analogue and digital transducer information and converting it to digital data to be sent to a computer or data acquisition system for examination and/or archiving. A power supply 90 ("External Power Supply") supplies power. In one aspect the data is sent via RS 232 or, alternatively, over a wireless connection using the wireless modem 84. The data transmission circuitry is set up as a population option where either the modem 84 or a daughter board (not shown) containing the RS 232 is populated. Used in conjunction with the GCIB's 81, the GCIB's interface via an interface 130 directly to the gas detectors 82 and perform the digitization of the sensor signals. Four connections to each sensor include power, ground, gas channel output, and reference channel output connections. A serial interface between the GCIB's 81 and the main board 83 is used The main board 83 handles temperature control of the unit and of the gas detectors 82. The case heater 105 is used to maintain a minimum unit temperature within the volume enclosed by the case to prevent the flame arrestors 87c from freezing. The flame arrestors have an intake 87A and an outlet 87B. The heaters dissipate heat directly to the required area when necessary. Whenever the temperature reported by the onboard temperature sensor 110 is below the specified threshold, the case heaters are enabled. The heater 87 and thermal electric cooler 88 control the temperature of the gas detectors 82 using the fan 95. Proportional-differential control ("Temperature Controls" 120) is used for the sensor temperature to enhance, and in one aspect to provide maximum stability, of the temperature. The temperature set point is specified, as well as a controller gain for both the heater and cooler (multiplier for the proportional term), and a single damping factor is applied to both the heater and cooler (multiplier for the differential term). Control values for temperature control of the unit are programmable via a microcontroller EEPROM 83c. The temperature control values can be set in the host laptop software and stored on the WSGD PCB microchip on the main board 83.

The main board 83 has three analogue to digital channels 131 that accept either a 4-20 mA or 2-5V analogue signal from external sources. There are outputs to drive the case and sensor heaters as well as the thermal electric cooler. The on-board temperature sensor in the Temperature Controls module 120 is interfaced through the analogue-to-digital converter on the main board 83.

An on-board PIC microcontroller 140 reads the data from the detectors 82, handles control of the unit and sensor temperatures, and performs some processing of the data, such as averaging it to improve the signal-to-noise ratio. It then transmits the sensor data to the host 85 via the wireless modem 84 (or via direct RS 232 link, not shown). The main board 83 can drive LEDs 133 to indicate the status of the card, main board processor and modem. Non-volatile memory 83a in the microcontroller 140 is used to store temperature control parameters, as well as the unit's gas calibration data required by the host application software 86 to convert the raw sensor readings into calibrated values. The cooler 88 cools the sensors and the power supply. In one aspect, the cooler fan 95 is on top of the cooler 88.

Referring to FIGS. 10, 11, 12 and 13 the sensor block of FIG. 9A is shown in more detail. Sensor block 150 comprises an aluminium body 151 in which two blind bores 152, 153 have been bored and provided with threads. The aluminium body 151 measures 70 mm (2.75") by 57 mm (2.25") by 22 mm (0.87") (L×W×H) and the holes 152, 153 each have a diameter of 17 mm (0.68") and a length of 44 mm (1.75"). The body 151 comprises two external ports 154 and an internal port 155 (see FIG. 13) that provide a path for gas through the aluminium body. In particular gas may flow from outside one side of the aluminium body 151, into the bore 152, through the internal port 155, into the bore 153 and out through the opposite side of the aluminium body 151. Two gas supply fittings 156, 157 are mounted at one end to the aluminium body 151 to a respective external port 154; the other end of each gas supply fitting may receive and mount a gas supply line (not shown).

Heaters/coolers 151a are mounted on three faces of the aluminium body 151. When passing a current the heaters/coolers 151a act as either a heat source or heat sink. The aluminium body 151 is good conductor of heat having a thermal conductivity of about 205 W m$^{-1}$ K$^{-1}$. Accordingly the temperature of the aluminium block 151a is readily controlled by the heaters/coolers 151a.

A methane sensor 158 is mounted in bore 152 and a propane sensor 159 is mounted in the bore 153, both held in position by means of threads that engage the threads in the aluminium body 151. Each sensor 158, 159 comprises a temperature sensor (not shown) sold under order number LM335 manufactured by National Semiconductor, Inc. Two electric cables 160, 161 provide power to the sensors and receive their output.

Figure 14:
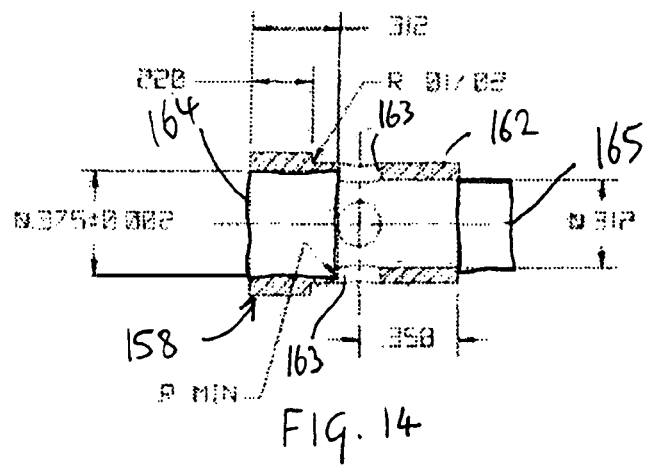
FIG. 14 is a side cross section through a methane light chamber according to the present invention.

Referring to FIG. 14 the propane sensor 159 comprises a generally cylindrical aluminium housing 162 provided with four ports 163 spaced equi-circumferentially at the same axial position along the housing 162. The ports 163 permit gas to flow into a light chamber defined by the housing 162. An IR emitter 164 is mounted at one end of the housing 162 and an IR detector 165 is mounted at the opposite end. The IR emitter and detector have a path length between them of 12.7 mm (0.5").

The IR emitter 164 comprises a Gilway Technical Lamp model #MR3-1150. This IR emitter has a relative spectral radiation of about 75% in the wavelength range of 3.2-4.0 µm i.e. covering the absorbance range of interest. The IR emitter 164 also comprises a parabolic reflector to help collimate the IR light toward the IR detector 165 during use.

The IR detector 165 comprises an Eltec Instruments, Inc. model #479 pyroelectric detector that has two channels: a reference channel and a detection channel. Each channel is provided with a filter and lithium tantalate crystal, the filter for filtering the wavelength band of interest.

Figure 16:
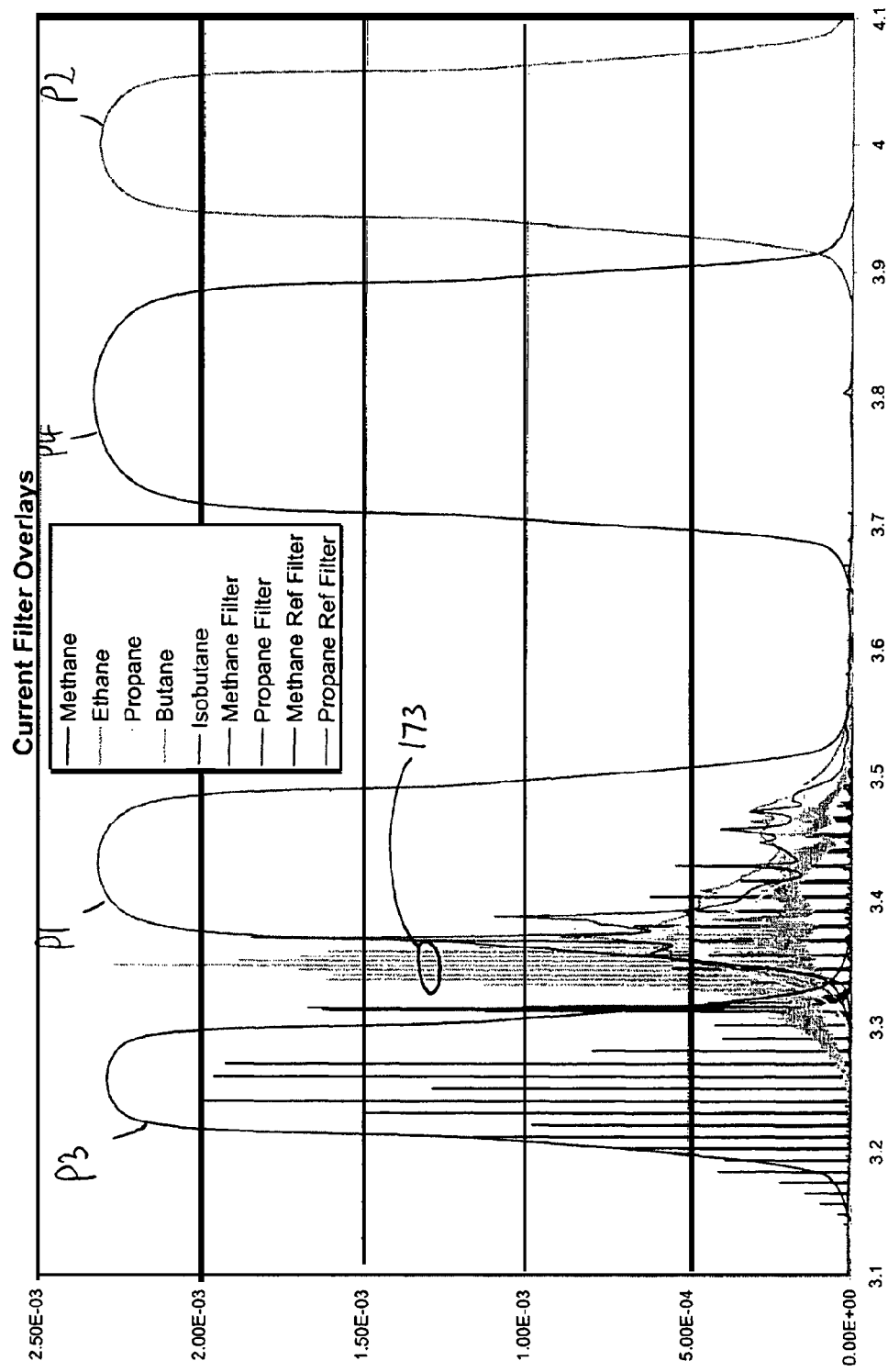
FIG. 16 is a graph of absorbance vs. wavelength for various hydrocarbons and the frequency passbands of filters used in the apparatus according to the present invention.

FIG. 16 shows the passbands of the filters. The propane detection filter over the detection channel crystal is made of quartz (fused silica) and has the following properties (passband P1 FIG. 16):

| | |
|---|---|
| Centre wavelength: | 3430 nm (tolerance < ±20 nm) |
| Half-power bandwidth: | 180 nm (tolerance < ±20 nm) |
| Passband transmission: | >70% |

A filter with these properties can presently be obtained from Spectrogon AB. The propane reference filter over the reference channel is an Eltec filter #570 (sapphire) and has the following properties (passband P2 FIG. 16):

| | |
|---|---|
| Centre wavelength: | 4000 nm (tolerance < ±25 nm) |
| Half-power bandwidth: | 120 nm (tolerance < ±20 nm) |
| Passband transmission: | >70% |

The tolerances mentioned above are to provide a guide for the use of alternative filters to the specific products mentioned.

Figure 15:
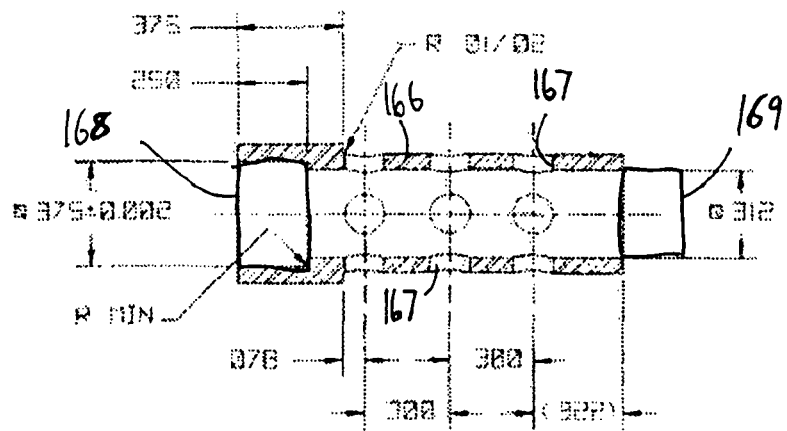
FIG. 15 is a side cross section through a propane light chamber according to the present invention.

Referring to FIG. 15 the methane sensor 158 comprises a generally cylindrical aluminium bushing 166 provided with twelve ports 167, in three groups of four each group of four being spaced equi-circumferentially around the housing 166. The ports 167 permit gas to flow into a light chamber defined by the housing 166. An IR emitter 168 is mounted at one end of the housing 166 and an IR detector 169 is mounted at the opposite end. The emitter and detector have a path length between them of 25.4 mm (1.0").

The IR emitter 168 comprises a Gilway Technical Lamp model #MR3-1088. This IR emitter has a relative spectral radiation of about 75% in the wavelength range of 3.2-4.0 µm i.e. covering the absorbance range of interest. The IR emitter 165 also comprises a parabolic reflector to help collimate the IR light toward the IR detector 169 during use.

The IR detector 169 comprises an Eltec Instruments, Inc. model #479 pyroelectric detector that has two channels: a reference channel and a detection channel. Each channel is provided with a filter and lithium tantalate crystal, the filter for passing the wavelength band of interest.

The methane detection filter over the detection channel crystal is made of quartz (fused silica) and has the following properties (passband P3 FIG. 16):

| | |
|---|---|
| Centre Wavelength: | 3260 nm (tolerance ±20 nm) |
| 5% cut-on: | 3190 nm (tolerance ±15 nm) |
| 5% cut-off: | 3330 nm (tolerance < ±10 nm) |
| Half-power bandwidth: | 93 nm |
| Passband transmission: | >70% |

The 5% cut-off wavelength is the most critical of the three parameters as will be explained in greater detail below. A filter with these properties can presently be obtained from Spectrogon AB. The methane reference filter over the reference channel is an Eltec filter #380 (sapphire) and has the following properties (passband P4):

| | |
|---|---|
| Centre wavelength: | 3800 nm (tolerance < ±40 nm) |
| Half-power bandwidth: | 180 nm (tolerance < ±20 nm) |
| Passband transmission: | >70% |

The tolerances mentioned above are to provide a guide for the use of alternative filters to the specific products mentioned.

Each IR detector 165, 169 is provided with a quartz window over both channels. The quartz window is substantially transparent to IR wavelengths in the region of interest.

In use sample gas is drawn with air at atmospheric pressure through the polyurethane line 37 into the wireless gas monitor 72 to the sensor block 150 (FIG. 9A) via a supply line (not shown). The gas passes into the aluminium block 151 via external port 154 and into the light chamber of the methane sensor defined by the housing 166. The sample gas exits the housing 166, passes through the internal port 155 and moves into the light chamber of the propane sensor defined by the housing 163. Finally the gas passes out of the other external port 154 and may be disposed of. Thus the sensor block provides for sample gas to be passed continuously through the two sensors without requiring valves or the like. Furthermore no special carrier gas is required and ambient air proximate the apparatus can be used.

As described above the main board 83 places each GCIB 81 into gas sample mode to determine if any detectable quantity of hydrocarbon gas is passing through the sensor block 10. Each IR emitter 164, 168 is driven by its corresponding GCIB 81 at 4.17 Hz with a voltage of approximately 4.5V and a duty cycle of 50%. Although the IR detectors 165, 169 are most sensitive at around 1 Hz, 4.17 Hz is used as it provides a faster response time to different gases passing through by the detectors. The driving frequency has no effect on the ability of different gases to be detected.

Thus infra-red light is emitted from each IR emitter 165, 169 in a cyclical manner into the respective light chamber defined by the housing 162 and housing 166. Due to the aforementioned parabolic reflector around each IR emitter 164, 168 the infra-red light travels substantially axially along the length each light chamber toward the corresponding IR detector. Any hydrocarbon gas present in one of the light chambers will absorb photons at wavelengths shown by the absorption spectra in FIG. 16. If any hydrocarbon gas is present the light reaching the detectors 165, 169 will be attenuated in intensity.

With no gas present in the light chambers, the pulses of IR light are received by the detectors 165, 169 substantially unchanged. Each pulse of IR light passes through the quartz window, some impinging on the reference channel and some impinging on the detection channel. The IR light is absorbed by the lithium tantalate crystal of each channel and an output voltage is produced that is proportional to the infra-red radiation intensity i.e. the amount of heat generated. Since the IR emitters 164, 168 are pulsed with a 50% duty cycle, each crystal is heated for 50% of the time and cools for 50% of the time. As the polarity of the charge on the crystal is positive for heating and negative for cooling the output from each channel of each detector is similar to a sine wave of 4.17 Hz frequency.

The amount of heating and cooling of the crystals is thus dependent on the intensity of IR radiation reaching them and therefore on the amount of IR radiation absorbed by any hydrocarbon gas in the light chambers. The magnitude of the output signal from the IR detectors 165, 169 changes according to the amount of gas in the light chambers.

Figure 17:
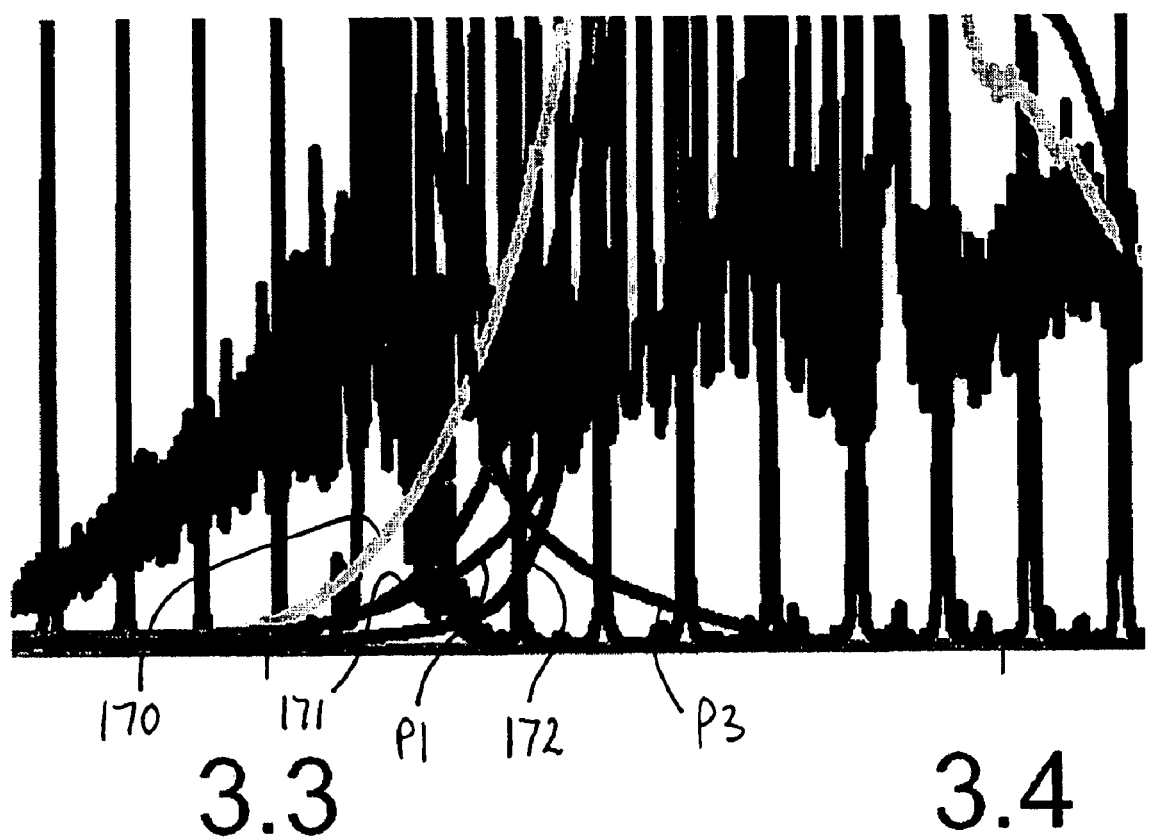
FIG. 17 is an expanded view of part of the graph of FIG. 16.

Each lithium tantalate crystal responds to incident radiation in any part of the spectrum. Therefore the aforementioned filters are chosen to select a portion of the spectrum of interest and reject the remainder. For the methane sensor 158, the wavelength range is as mentioned above. It will be seen in FIG. 16 that a portion of the methane absorption spectrum between about 3150 nm and about 3330 nm is separated from the other hydrocarbons. The methane detection filter passes IR light in this wavelength range. As mentioned above the 5% cut-off (i.e. the upper wavelength limit) is of importance. Referring to FIG. 17 a close-up of the 5% cut-off shows that the absorption spectrum of propane 170, butane 171 and isobutane 172 becomes more significant from about 3340 nm upwards. The methane detection filter has a 5% cut-off at 3330 nm so that the effect of these heavier hydrocarbons is reduced in the methane sensor output.

Regarding the propane detection filter it will be seen in FIG. 17 that there is a peak 173 in the ethane absorption spectrum between approximately 3330 nm and 3355 nm. However, it will also be seen that the absorption spectra of the heavier hydrocarbons (including propane) becomes significant at about 3350 nm. Accordingly the 5% cut-on (i.e. the lower wavelength limit) of the propane detection filter must be selected carefully to reject the ethane absorption peak 173 but pass as much of the heavier hydrocarbon absorption wavelengths as possible. The range of the propane detection filter extends over the absorption range of the heavier hydrocarbons (propane, butane, isobutane) as described above. Although the ethane absorption spectrum also extends into this region its absorbance is low compared to the peak 173. Furthermore ethane is usually only present in wells in small proportions compared to methane e.g. a well might be 94% methane with the remaining 6% made up of ethane and heavier hydrocarbons.

As mentioned above the distance between the IR emitter and detector is different as between the methane sensor 158 and the propane sensor 159. Furthermore the IR emitter 164 in the methane sensor 158 is higher power than the IR emitter 168 in the propane sensor 159. As shown in FIG. 16 the methane absorption spectrum is comb-like in nature having discrete absorption peaks. Accordingly, although the absorption peaks are relatively high, the amount of IR light absorbed across the methane detection filter wavelength range is relatively low. In contrast, the absorption spectra of propane, butane and isobutane are each continuous, but relatively low in intensity compared to methane. The IR light travels a longer path length (25.4 mm) to provide an improved IR detector response over the range 0.01 to 100% by volume; the methane IR emitter 164 is therefore more powerful to provide an adequate signal level to the electronics. The IR light is provided with a shorter path length (12.7 mm) as the intensity will drop off faster in the presence of the heavier hydrocarbons due to their continuous spectra; as the path length is shorter a lower power IR emitter can be used.

The output signal from the methane sensor 158 and the propane sensor 159 is in analogue form. Each output signal is passed straight to the corresponding GCIB 81 where it passes through a low noise amplifier of gain 10, then through a gain stage of 6, 12, 24, or 48 times gain. This provides flexibility for use with different combinations of detectors and signal inputs. Each signal is then rectified, inverted and filtered to generate a DC voltage that increases with increasing gas in each sensor (i.e. decreasing IR light received at each detector). The DC voltage is then A/D converted. Early conversion to the digital domain helps to reduce the effect of temperature variation (see below). In particular, each GCIB 81 performs 4096 A/D conversions over a 1.2 s period per channel. The 4096 samples are then summed and averaged to generate an average value. Since the 4096 samples cover exactly 5 periods the IR emitter frequency, a null is formed at 4.17 Hz effectively removes all ripple at this frequency. The main board 83 then reads the average value for each sensor.

The main board 83 then places each GCIB 81 in temperature sample mode and reads the sensor temperature data and GCIB temperature data. The main board 83 uses the average value and temperature data to determine sensor data representing the actual percentage by volume of detectable gas in the methane sensor 158 and the propane sensor 159 respectively (described in greater detail below). The sensor data is then transmitted wirelessly to the host 85 for display, storage in memory and analysis by geologists. The main board places the GCIBs into gas and temperature sample mode every two seconds thereby providing substantially continuous output signal representing the presence of any light and heavy hydrocarbon gases in the methane sensor 158 and in the propane sensor 159.

Pyroelectric sensors exhibit a number of anomalies the most prominent being sensitivity to ambient temperature changes. Whilst measures described above are taken to keep the ambient temperature of the sensors relatively constant, it is necessary to ensure that the output from the sensors reflects primarily presence of gas and not ambient temperature changes. This is particularly important as the detector is required to work in a variety of extreme environments, many of which have large diurnal temperature ranges. For example, if the temperature within the detector enclosure increases, the temperature of the lithium tantalate crystal will also increase. Therefore the temperature difference of the crystal between IR emitter on and off will decrease, and the output from the sensor will decrease falsely indicating more gas in the sensors. Furthermore the crystals are also sensitive to the rate of change of temperature.

To counteract this effect the Eltec 479 sensors are provided with the aforementioned reference channel. The reference channel is parallel opposed to the detection channel whereby the reference channel is subtracted from the detection channel. Therefore any sudden temperature variation is compensated to some extent, but gradual changes in ambient temperature are not compensated. The methane reference filter (with properties described above) is selected to pass a portion of the spectrum that is substantially unaffected by the absorption spectra of the hydrocarbons of interest and is therefore outside the 3.1-3.6 µm range. The fact that there is some very small amount of absorption by heavier hydrocarbons in the methane reference filter passband means that in the absence of any methane, the response of the methane sensor 158 will go slightly negative if any heavier hydrocarbons are present. This has not been found problematic. The propane reference filter is chosen in a similar manner, although needs to avoid the absorption by heavier hydrocarbons in the 3.8 µm range.

It will be noted from the specifications given above that the material of the detection channel filters (quartz) differs from the reference channel filters (sapphire). The applicant has found, due to the differing thermal conductivities, a very rapid change in sample gas temperature generates different responses from the two channels and therefore erroneous sensor output. It was found that a sudden pressure change of the sample gas was enough to generate a rapid temperature change and to see this effect. The applicant solved this problem by improving thermal isolation of each IR detector 165, 169 by placing the aforementioned quartz window over both channels.

Each GCIB 81 is also sensitive to temperature and for improved accuracy the applicant has provided compensation for this variation.

The temperature sensitivity of both the IR detectors 165, 169 and the GCIB 81 analogue electronics are primarily dependent on the overall gain of the GCIB analogue channels. Reducing the gain of this stage reduces any temperature effects, allowing the apparatus to work accurately in a wider range of operating temperatures. However, reducing the gain reduces the resolution and therefore sensitivity of the apparatus to gas. These two competing needs must be balanced. The GCIB A/D converter has a range of 0 to 65535 and the temperature sensitivity of the IR detectors 165, 169 is in the range 200 to 500 A/D values per ° C.; the GCIB temperature sensitivity is about 0 to 30 A/D values per ° C., dependent on gain setting. The offset (zero) is chosen between 18000 and 20000 A/D values when the operating temperature is about 30° C. The gain (span) of the each IR detector is set to between 25000 and 30000 A/D values. This gives reasonable resolution and an operating temperature range of −5° C. to 50° C.

Calibration of each gas sensor takes place in two stages: temperature compensation and gas calibration.

Temperature Compensation

Temperature compensation converts raw A/D values into temperature invariant values that are nominally equal to zero with no detectable gas in the detector; these values will be referred to as compensated A/D values.

For the dual channel Eltec 479 sensor, both channels will respond in a similar way to temperature transients. However, they may have differing sensitivities to ambient temperature. Firstly, the reference channel is used to remove variations in detection channel data caused by temperature transients. Reference channel data are plotted against detection channel data in x-y format to ascertain the linear relationship between them. The gradient of this relationship is the reference gain difference (RGD) between the two channels. Therefore, multiplying the reference channel by the RGD and subtracting the result from the detection channel should remove effects caused by any temperature transients. The result of this is called the reference compensated A/D value (RCV).

The next step is to adjust the RCV for temperature. This is done by subtracting from the RCV a number of A/D values representing the effect of current temperature on the IR detectors 165, 169 and GCIBs 81. This scaling value is therefore a function of temperature. To determine the number of A/D values to subtract different RCVs are plotted against a weighted average of the sum of IR detector and GCIB temperatures (e.g. w×IR detector temperature+(1−w)×GCIB temperature, $0 \leq w \leq 1$). The weighting w and the RGD are then varied to make the relationship between temperature and RCVs as close to linear as possible. Once substantially linear, the gradient G of the relationship represents a constant rate of change of RCV (or A/D values) with temperature. Therefore to determine a temperature compensated A/D value (TCV) using the gradient G it is necessary to determine the offset $T_{offset}$ that represents the RCV value at T=0° C. A TCV can then be obtained as follows:

$$TCV_{dual} = RVC - (wGT_{detector} + (w-1)GT_{GCIB} + T_{offset})$$

In this way when there is zero detectable gas in either of the detectors, the TCV should be roughly zero independent of operating temperature and temperature transients.

If a single channel IR detector is used temperature compensation is based only on the sensor and GCIB 81 temperatures. A linear scaling is used for both temperatures, and there is a single offset value used in the compensation. The TCV for a single channel sensor is given by:

$$TCV_{single} = \text{Raw A/D value} - (Scale_{sensor} \times T_{sensor} + Scale_{GCIB} \times T_{GCIB} + T_{Offset})$$

Gas Calibration

Having been temperature compensated the outputs from the IR detectors 164, 168 should depend primarily only on the amount of detectable gas in the each of the sensors 158, 159. In theory, there is an inverse logarithmic relationship between the amount of detectable gas in the light path and the amount of light that reaches the IR detectors 165, 169. However, the actual response is not strictly logarithmic due to a number of factors including multiple path lengths within each sensor, non-ideal sensor and circuit response. The actual response of the sensor to the target gas is non-linear whilst the aim is to achieve a substantially linear response between 0.01% and 100% detectable gas by volume: the IR detector output changes most rapidly at low gas concentrations, and becomes less sensitive as concentration increases. Accordingly, to calibrate the apparatus different concentrations of methane and propane gas are each run through the detectors and a polynomial fitted to a graph of output TCVs vs. gas concentration. Although other hydrocarbons affect the response of the pyroelectric detectors to some extent in the wavelength ranges selected above, in the applicant's experience the proportion of methane and propane in a well is much higher than any of the other hydrocarbons. Therefore the sensors are calibrated for one hydrocarbon gas respectively. In this way the wireless gas monitor 72 enables the petroleum geologist to distinguish between light and heavy hydrocarbons in the well, as well as receiving a total gas indication as a percentage by volume.

For light hydrocarbon (methane and ethane) detection it has been found that a fifth order polynomial of the form $y = Ax^5 + Bx^4 + Cx^3 + Dx^2 + Ex + F$ fits the data well. The constants A to F are dependent on the particular detector/GCIB combination and are readily determined from the results.

For heavier hydrocarbon (i.e. propane, butane, isobutane) detection the applicant has found that a fifth order polynomial does not fit the results well over the range of 0-100% concentration. A fifth order polynomial of the form $y = Gx^5$ fits the data well between 0% and 30% concentration, whilst a fourth order polynomial of the form $y = Hx^4 + Ix^3 + Jx^2 + Kx + L$ fits the data well between 30% and 100%. The constants G to L are dependent on the particular detector/GCIB combination and are readily determined from the results.

Once determined for each detector/GCIB combination, the polynomials and constants are stored in memory either on the remote host 85 or on the wireless portable gas monitor 72. During use, as each TCV is received the methane or propane polynomial is used to determine the corresponding gas concentration. This result is then stored in memory for onward transmission to the host 85 as described above.

The TCVs should always be about the same for a certain gas concentration, providing the pressure and temperature of the gas remain the same. Therefore during calibration the sample gas should be kept close to atmospheric pressure.

Figure 18:
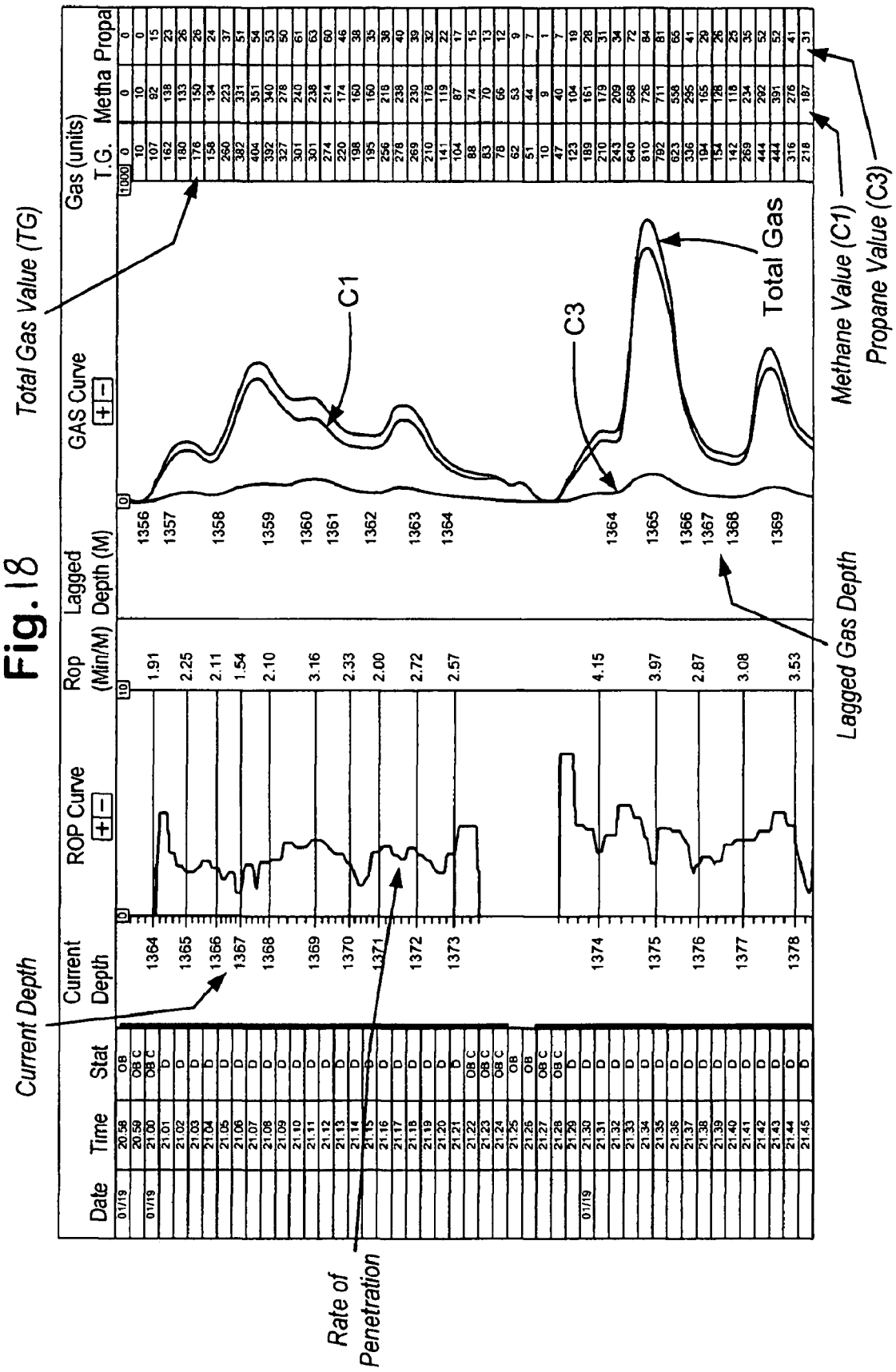
FIG. 18 is a typical display on a remote host of the output received from the apparatus of FIGS. 9A and 9B.

FIG. 18 shows one typical display produced on the host 85 when it receives data wirelessly from the wireless portable gas monitor 72. One curve indicates methane ("C1"); one curve indicates propane ("C3") and one curve indicates total gas content ("TOTAL GAS"). Total gas can be determined by summing the outputs from the methane and propane sensors and dividing by two. A numerical read out NR indicates total gas ("T.G."); methane content ("Metha"); and propane content ("Propa"). The date is indicated in the DATE column and the time (actual real time) is indicated in minute increments in the TIME column. The curves and the numerical read outs correspond to real times in the TIME column and to actual depths in the DEPTH column. Rate of penetration of the drill bit for increasing depths is indicated by the ROP curve.

It is envisaged that more than one sensor block 150 may be mounted in the wireless portable gas monitor 72. Furthermore it may be possible to replace the two, two channel IR detectors with one four channel IR detector comprising three gas detection channels and one reference channel. Alternatively a single channel IR detector may be used with appropriate temperature compensation as described above. Any IR detector with adequate sensitivity (e.g. thermopiles) may be used in place of the pyroelectric detectors described in the specific embodiment.

Instead of transmitting TCVs the wireless portable gas monitor 72 may transmit raw data (comprising either RCVs or raw A/D values, and temperature data) for subsequent processing by the remote host 85. For example, the remote host 85 may store the polynomial coefficients and use the formulae described above to calculate TCVs (either dual or single) for display and/or storage.

The present invention, therefore, in at least some, but not necessarily all embodiments, provides a method for detecting gas in a fluid, the method including flowing fluid bearing gas through a gas trap apparatus, flowing gas trapped by the gas trap apparatus to and through an infra-red gas detection system for detecting the gas, the infrared gas detection system having a first processor and apparatus for isolating absorption spectra of the gas, producing with the infra-red gas detection system analogue signals indicative of levels of the gas, converting the analogue signals to digital signals with the first processor, transmitting the digital signals from the first processor to a second processor, and producing with the second processor digital signals indicative of the level of gas. Such a method may have one or some (in any possible combination) of the following: wherein the fluid is drilling fluid and the gas is hydrocarbon gas from a wellbore; wherein the analogue signals are transmitted wirelessly; producing with the second processor a visual display (screen, strip chart) of a level of the gas; wherein the production of the analogue signals and the production of the digital signals is done in real time; wherein the first processor includes an interface board for receiving the analogue signals, for converting the analogue signals to the digital signals, and for then transmitting the digital signals to the second processor, the second processor including a host computer for receiving the digital signals and for processing the digital signals to produce an indication of level of the gas, the method further including the interface board receiving the analogue signals and converting the analogue signals to the digital signals, the interface board transmitting the digital signals to the host computer, and producing with the host computer an indication of the level of the gas; wherein the host computer produces an indication of a level of total gas in the fluid and/or displays said indication; wherein the interface board has a programmable medium programmed to calibrate the infra-red gas detection system and the method further including calibrating the infra-red gas detection system with the interface board; wherein the host computer provides a user interface for conducting the method; conditioning the analogue signals with the interface board to reduce noise in said signals; wherein the infra-red gas detection system has gas sensor apparatus and there is no physical reaction between the gas and the gas sensor apparatus; controlling temperature of the infra-red gas detection system; wherein the infra-red gas detection system includes the first processor and the infra-red gas detection system is in an enclosure and heater apparatus and cooling apparatus are connected to the enclosure for controlling temperature therein; wherein the infra-red gas detection system is portable; wherein the gas is hydrocarbon gas; wherein the hydrocarbon gas is methane and/or propane; wherein the infra-red gas detection system includes a gas detector with a detection channel and a reference channel, the method further including detecting with the detection channel infra-red radiation absorbed by the gas, and compensating with the reference channel for variations in the gas; filtering moisture from the gas prior to flowing the gas to the infra-red gas detection system to inhibit or prevent the generation of false readings due to moisture; and/or wherein the infra-red gas detection system includes an infra-red lamp, an infra-red lamp drive, and a gas sensor and the interface board provides an interface between the infra-red lamp drive and the gas sensor.

The present invention, therefore, in at least some, but not necessarily all embodiments, provides a method for detecting gas in drilling fluid, the method including flowing drilling fluid bearing hydrocarbon gas from a wellbore through a gas trap apparatus; flowing gas trapped by the gas trap apparatus to and through an infra-red gas detection system for detecting the hydrocarbon gas, the infrared gas detection system having narrow band infrared filter apparatus for isolating absorption spectra of the hydrocarbon gas; producing with the infra-red gas detection system analogue signals indicative of levels of the hydrocarbon gas; transmitting the analogue signals to a first processor for converting the analogue signals to digital signals; transmitting the digital signals from the first processor to a second processor, producing with the second processor digital signals indicative of the level of hydrocarbon gas; the first processor including an interface board for receiving the analogue signals, for converting the analogue signals to the digital signals, and for then transmitting the digital signals to the second processor; the second processor including a host computer for receiving the digital signals and for processing the digital signals to produce an indication of level of the gas; the method further including the interface board receiving the analogue signals and converting the analogue signals to the digital signals; the interface board transmitting the digital signals to the host computer; producing with the host computer an indication of the level of the gas; wherein the infra-red gas detection system has gas sensor apparatus and there is no physical reaction between the gas and the gas sensor apparatus; controlling temperature of the infra-red gas detection system; wherein the infra-red gas detection system includes the first processor and the infra-red gas detection system is in an enclosure and heater apparatus and cooling apparatus are connected to the enclosure for controlling temperature therein.

The present invention, therefore, in at least some, but not necessarily all embodiments, provides a system for detecting gas in a fluid, the system including an enclosure; an infra-red gas sensor apparatus within the enclosure; an interface board apparatus within the enclosure and in communication with the infra-red gas sensor apparatus; analogue signal apparatus in the infra-red gas sensor apparatus for producing analogue signals indicative of a level of gas in a fluid; conversion apparatus on the interface board apparatus for converting the analogue signals to digital signals; and transmission apparatus on the interface board apparatus for transmitting the digital signals to a host system.

The invention claimed is:

1. A method of detecting gas conveyed in a drilling fluid returning from a well, which method comprises the steps of: (a) extracting gas from said drilling fluid; (b) transmitting infra-red radiation through said gas; and (c) detecting with a detector infra-red radiation that has passed through said gas and providing an output signal representative thereof; characterized by the step of: (d) examining the intensity of a portion of the infra-red spectrum within a range of approximately 3.1 .mu.m and 3.6 .mu.m to estimate whether or not said gas comprises any light or heavy hydrocarbons, and wherein step (b) comprises driving an infra-red emitter in a cyclical manner so as to produce pulses of infra-red radiation, whereby a cyclical output voltage corresponding to said pulses is obtained from said detector the magnitude of which represents the intensity of infra-red radiation received by said detector, and wherein said driving comprises driving said infra-red emitter with a 50% duty cycle, whereby an output from said infra-red detector is substantially sinusoidal, and converting said cyclical output voltage to DC, the magnitude of which is proportional to the amount light or heavy hydrocarbon present in said gas.

2. A method according to claim 1, wherein said portion comprises part of an absorption spectrum of a light hydrocarbon, and wherein said portion comprises an upper wavelength limit of approximately 3330 nm to reduce detection of heavy hydrocarbons, and wherein said portion comprises a lower wavelength limit of approximately 3190 nm.

3. A method according to claim 1 wherein said portion comprises a lower wavelength limit of approximately 3340 nm to reduce detection of light hydrocarbons, and wherein said portion comprises an upper wavelength limit of approximately 3540 nm.

4. A method according to claim 1 further comprising the steps of transmitting infra-red light through said gas over a first path and over a second path shorter than said first path, and outputting a signal representing the intensity of infra-red light received over each path, and the step of examining a first portion in said range for infra-red light received on said first path, and a second portion in said range for infra-red light received on said second path, wherein said first and second portions are different to distinguish between any light and heavy hydrocarbons in said gas.

5. A method according to claim 1 further comprising the steps of measuring said intensity with a pyroelectric detector, and the step of substantially thermally isolating said pyroelectric detector from said gas, whereby the effect of pressure and/or temperature variation of said gas on said output signal is reduced.

6. A method according to claim 1 further comprising the step of outputting a reference channel, which reference channel represents an infra-red radiation intensity at a wavelength outside said range, whereby said reference channel may be used to adjust said output signal such that it is substantially temperature invariant, and the step of subtracting said reference channel from said output signal to remove any temperature transients therefrom, and the step of multiplying said reference channel by a scaling factor before said subtraction step to compensate for any difference in response of said detector and said reference channel to temperature variation.

7. A method according to claim 1, further comprising the step of repeating steps (a) to (d) to provide a substantially continuous output signal representing the amount of light and heavy hydrocarbons contained in said drilling fluid, and the step of averaging said output signal over a predetermined time period.

8. A method according to claim 1, further comprising the step of transmitting data representing said output signal to a remote host, said data useable by said remote host to display a substantially real-time indication of the amount of light and heavy hydrocarbons present in said drilling fluid and/or a total hydrocarbon gas content present in said drilling fluid.

9. A method according to claim 1, wherein said infra-red detector comprises a pyroelectric crystal, said method further comprising the steps of monitoring a temperature environment around said infra-red detector, and heating or cooling said environment according to said temperature.

10. A method according to claim 1, wherein said light hydrocarbon comprises methane and/or ethane, and wherein said heavy hydrocarbon comprises propane and/or butane and/or pentane.

* * * * *